United States Patent
Alter

(10) Patent No.: US 10,610,556 B2
(45) Date of Patent: Apr. 7, 2020

(54) COMPOSITIONS FOR REGULATION AND CONTROL OF APPETITE

(71) Applicant: Therapeutic Solutions LLC, Newark, DE (US)

(72) Inventor: Sue Ann Alter, Encino, CA (US)

(73) Assignee: Therapeutic Solutions LLC, Newark, DE (US)

( * ) Notice: Subject to any disclaimer, the term of this patent is extended or adjusted under 35 U.S.C. 154(b) by 0 days.

(21) Appl. No.: 14/857,797

(22) Filed: Sep. 17, 2015

(65) Prior Publication Data

US 2017/0080037 A1 Mar. 23, 2017

(51) Int. Cl.

| | |
|---|---|
| A61K 45/06 | (2006.01) |
| A61K 36/258 | (2006.01) |
| A61K 31/137 | (2006.01) |
| A61K 31/198 | (2006.01) |
| A61K 31/405 | (2006.01) |
| A61K 31/4415 | (2006.01) |
| A61K 31/522 | (2006.01) |
| A61K 31/714 | (2006.01) |
| A61K 33/06 | (2006.01) |
| A61K 33/24 | (2019.01) |
| A61K 36/41 | (2006.01) |
| A61K 36/481 | (2006.01) |
| A61K 36/67 | (2006.01) |
| A61K 36/88 | (2006.01) |

(52) U.S. Cl.
CPC .......... *A61K 36/258* (2013.01); *A61K 31/137* (2013.01); *A61K 31/198* (2013.01); *A61K 31/405* (2013.01); *A61K 31/4415* (2013.01); *A61K 31/522* (2013.01); *A61K 31/714* (2013.01); *A61K 33/06* (2013.01); *A61K 33/24* (2013.01); *A61K 36/41* (2013.01); *A61K 36/481* (2013.01); *A61K 36/67* (2013.01); *A61K 36/88* (2013.01); *A61K 45/06* (2013.01)

(58) Field of Classification Search
CPC .... A61K 36/258; A61K 31/198; A61K 36/48; A61K 33/06; A61K 45/06
USPC ....................................................... 514/690
See application file for complete search history.

(56) References Cited

U.S. PATENT DOCUMENTS

| 8,197,860 B2 | 6/2012 | Lin et al. |
|---|---|---|
| 8,318,807 B2 | 11/2012 | Schultheiss et al. |
| 8,399,712 B2 | 3/2013 | Schultheiss et al. |
| 8,415,507 B2 | 4/2013 | Schultheiss et al. |
| 8,513,236 B2 | 8/2013 | Schultheiss et al. |
| 8,563,609 B2 * | 10/2013 | Miller ..................... A23L 33/15 514/558 |
| 2004/0198754 A1 | 10/2004 | McKee et al. |
| 2006/0293255 A1 | 12/2006 | Lin et al. |
| 2007/0237786 A1 | 10/2007 | Heuer |
| 2010/0151058 A1 | 6/2010 | Cappello |
| 2011/0236512 A1* | 9/2011 | Kitazawa .............. A61K 31/132 424/750 |
| 2015/0099032 A1* | 4/2015 | Roumayeh .............. A23L 33/40 426/2 |
| 2015/0104523 A1 | 4/2015 | Lockwood |
| 2015/0157672 A1* | 6/2015 | Cairns .................... A61K 36/03 424/195.17 |

FOREIGN PATENT DOCUMENTS

| CN | 103918746 | 6/2015 |
|---|---|---|
| KR | 20130011110 | 1/2013 |
| WO | WO 2010141107 | 12/2010 |

OTHER PUBLICATIONS

Shanti et al, title: Herbal Medicines for Depression and Anxiety: A Comprehensive State of the Art Review, Global J Res. Med. Plants & Indigen. Med., vol. 2(5): 317-336, May 2013.*
Bionorica, product information of Echinapret®, available May 25, 2011.*
Author: unknown; Title: Why stress causes people overeat?, Harvard Mental Health Letter, published Feb. 2012.*
Author: Kim; Title: Chemical diversity of Panax ginseng . . . , J. Ginseng Res, vol. 36, No. 1, pp. 1-15; published 2012.*
Shanti, P.; title: Herbal Medicines for Depression and Anxiety: A Comprehensive State of the Art Review; Global J Res. Med. Plants & Indigen. Med.; vol. 2, Issue 5; pp. 317-336; May 2013. (Year: 2013).*
Author: unknown; Title: Why stress causes people overeat?, Harvard Mental Health Letter, published by Harvard health publishing on Feb. 2012.*
Acheson KJ, et al., Caffeine and Coffee: Their Influence on Metabolic Rate and Substrate Utilization in Normal and Obese Individuals. Am. J. Clin. Nutr. 1980; 33(5):989-97. Adam TC, et al., Stress, Eating and the Reward System. Physiol Behav. 2007;91(4):449-58. Akhondzadeh S, et al., Comparison of Crocus Sativus L. and Imipramine in the Treatment of Mild to Moderate Depression: A Pilot Double-Blind Randomized Trial. BMC Complement. Alt. Med. 2004;4:12.

(Continued)

*Primary Examiner* — Yanzhi Zhang
(74) *Attorney, Agent, or Firm* — Monique A. Vander Molen

(57) ABSTRACT

Compositions for appetite control and/or regulation or loss of weight are described. The described compositions comprise a unique combination of ingredients, the combination including at least botanical substances, amino acids, and one or more metals, and may comprise and in some embodiments do further comprise one or more vitamins and/or caffeine. The compositions are taken by mouth and provide a multi-targeted approach for the regulation and control of appetite for subjects taking the composition. The composition is preferably taken before a meal. A recommended dose includes at least one dose of the described composition per day.

23 Claims, No Drawings

(56) References Cited

OTHER PUBLICATIONS

Albert PR, et al. The Neurobiology of Depression—Revisiting the Serotonin Hypothesis. I. Cellular and Molecular Mechanisms. Philos. Trans. R. Soc. Lond. B Biol. Sci. 2012;367(1601):2378-81.
Andersen, T., et al., Weight Loss and Delayed Gastric Emptying Following a South American Herbal Preparation in Overweight Patients. J. Hum. Nutr. Diet, 2001;14(3):243-50.
Anton SD, et al., Effects of Chromium Picolinate on Food Intake and Satiety. Diabetes Technol. Ther. 2008;10(5):405-12.
Astrup A, et al., Caffeine: A Double-Blind, Placebo-Controlled Study of its Thermogenic, Metabolic, and Cardiovascular Effects in Healthy Volunteers. Am J Clin Nutr. 1990;51(5):759-67.
Avena NM, et al., Sugar and Fat Bingeing Have Notable Differences in Addictive-Like Behavior. J Nutr 2009;139(3):623-628.
Azizov AP, Seifulla RD, The effect of elton, leveton, fitoton, and adapton on the work capacity of experimental animals. Eksp. Klin. Farmakol. 1998;61(3):61-3.
Balk EM, et al., Effect of Chromium Supplementation on Glucose Metabolism and Lipids: A Systematic Review of Randomized Controlled Trials. Diabetes Care Aug. 2007;30(8):2154-63.
Ballinger AB, et al., L-Phenylalanine Releases Cholecystokinin (CCK) and Is Associated With Reduced Food Intake in Humans: Evidence for a Physiological Role of CCK in Control of Eating. Metabolism Jun. 1994 ;43(6):735-8.
Baltaci D, et al., Association of Vitamin B12 with Obesity, Overweight, Insulin Resistance and Metabolic Syndrome, and Body Fat Composition; Primary Care-Based Study. Med Glas (Zenica) 2013;10(2):203-10.
Banderet LE, Leiberman HR. Treatment with tyrosine, a neurotransmitter precursor, reduces environmental stress in humans. Brain Res. Bull. 1989;22:759-762.
Barwell CJ, et al., Deamination of Hordenine by Monoamine Oxidase and its Action on Vasa Deferentia of the Rat. J. Pharm. Pharmacol. 1989;41(6):421-3.
Beckmann H, et al., L-Phenylalanine Versus Imipramine: A Double-Blind Controlled Study. Arch Psychiatr Nervenkr 1979;227:49-58.
Bell A, et al., A Look at Nutritional Supplement Use in Adolescents. J. Adolesc. Health 2004;34(6):508-16.
Berlan M, et al., Alpha 2-Adrenoceptor Antagonist Potencies of Two Hydroxylated Metabolites of Yohimbine. Br. J. Pharmacol. 1993;108(4):927-32.
Bjorntorp P, et al., "Consolatory Eating" is Not a Myth. Stress-Induced Increased Cortisol Levels Result in Leptin-Resistant Obesity. Lakartidningen. 2001;98:5458-61.
Bleich S, et al., Why Is the Developed World Obese? Annu Rev Public Health 2008;29:273-95.
Blumenthal SR, et al., An electronic health records study of long-term weight gain following antidepressant use. JAMA Psychiatry 2014;71(8):889-96.
Boon-Niermeijer EK, et al., Phyto-Adaptogens Protect Against Environmental Stress-Induced Death of Embryos From the Freshwater Snail Lymnaea Stagnalis. Phytomedicine 2000;7:389-399.
Brown D, et al., Natural Remedies for Depression. Nutr. Sci. News Feb. 1999.
Brown CM, et al., Activities of Octopamine and Synephrine Stereoisomers on Alpha-Adrenoceptors. Br. J. Pharmacol. 1988;93(2):417-29.
Cangiano C, et al., Eating Behavior and Adherence to Dietary Prescriptions in Obese Adult Subjects Treated With 5-Hydroxytryptophan. Am J Clin Nutr 1992;56:863-867.
Carpene, C, et al., Selective Activation of beta3-Adrenoreceptors by Octopamine: Comparative Studies in Mammalian Fat Cells. Naunyn Schmiedebergs Arch Pharmacol. 1999;359(4):310-21.
Chadwick D, et al., Manipulation of Brain Serotonin in the Treatment of Myoclonus. Lancet 1975;2:434-435.
Chapman C, et al., Lifestyle Determinants of the Drive to Eat: A Meta-Analysis. Am. J. Clin. Nutr. 2012;96(3):492-7.
Crawford V, et al., Effects of Niacin-Bound Chromium Supplementation on Body Composition in Overweight African-American Women. Diabetes Obes Metab, 1999;1(6):331-337.
Darbinyan V, et al., Clinical Trial of Rhodiola rosea L. Extract SHR-5 in the Treatment of Mild to Moderate Depression. Nord J Psychiatry. 2007;61(5):343-8.
Davis BA, et al., Correlations of Plasma and Urinary Phenylacetic Acid and Phenylethylamine Concentrations with Eating Behavior and Mood Rating Scores in Brofaromine-Treated Women with Bulimia Nervosa. J. Psychiatry Neurosci. 1994;19(4):282-8.
Deijen JB, et al., Tyrosine Improves Cognitive Performance and Reduces Blood Pressure in Cadets After One Week of a Combat Training Course. Brain Res. Bull. 1999;48 (2):203-9.
Den Boer JA, Westenberg HG, Behavioral, Neuroendocrine, and Biochemical Effects of 5-Hydroxytryptophan Administration in Panic Disorder. Psychiatry Res 1990;31:267-278.
Desbrow B, et al., The Effects of Different Doses of Caffeine on Endurance Cycling Time Trial Performance. J. Sports Sci. 2012;30(2):115-20.
Detillion CE, et al., Social Facilitation of Wound Healing. Psychoneuroendocrinology 2004;29(8):1004-11.
Docherty JP, et al., A Double-Blind, Placebo-Controlled, Exploratory Trial of Chromium Picolinate in Atypical Depression: Effect on Carbohydrate Craving. J Psychiatr Pract. 2005;11(5):302-14.
Dodge TL, Jaccard, JJ, The Effect of High School Sports Participation on the Use of Performance-Enhancing Substances in Young Adulthood. J. Adolesc. Health 2006;39(3):367-73.
Douglas AJ, Central Noradrenergic Mechanisms Underlying Acute Stress Responses of the Hypothalamo-Pituitary-Adrenal Axis: Adaptations Through Pregnancy and Lactation. Stress 2005;8(1):5-18.
Dourish CT, Boulton AA, The Effects of Acute and Chronic Administration of Beta-Phenylethylamine on Food Intake and Body Weight in Rats. Prog. Neuropsychopharmacol. 1981;5(4):411-4.
Dulloo AG, et al., Efficacy of a Green Tea Extract Rich in Polyphenols and Caffeine in Increasing 24-hr Energy Expenditure and Fat Oxidation in Humans. Am. J. Clin. Nutr. 1999; 70(6):1040-5.
Dulloo AG, et al. Normal Caffeine Consumption: Influence on Thermogenesis and Daily Energy Expenditure in Lean and Postobese Human Volunteers. Am. J. Clin. Nutr. 1989;49(1):44-50.
Dulloo AG, et al., Green Tea and Thermogenesis: Interactions Between Catechin-Polyphenols, Caffeine and Sympathetic Activity. Int J Obes Relat Metab Disord. 2000;24(2):252-8.
Edamula R, et al., Prenatal Developmental Toxicity of Crocus Sativus (Saffron) in Wistar Rats. Int. J. Pharmacol. and Toxicol. 2014;2(2):46-49.
Edwards D, et al., Therapeutic Effects and Safety of Rhodiola Rosea Extract WS 1375 in Subjects With Life-Stress Symptoms—Results of an Open-Label Study. Phytother Res. Aug. 2012;26(8):1220-5.
Ettehadi H, et al., Aqueous Extract of Saffron (*Crocus sativus*) Increases Brain Dopamine and Glutamate Concentrations in Rats. J. Behavior. Brain Sci. 2013;3:315-319.
Fischer E, et al., Therapy of Depression by Phenylalanine. Preliminary Note. Arzneimittelforschung 1975;25:132.
Fugh-Berman A, Myers A, Citrus Aurantium, an Ingredient of Dietary Supplements Marketed for Weight Loss: Current Status of Clinical and Basic Research. Exp. Biol. Med. (Maywood) 2004;229(8):698-704.
5-Hydroxytryptophan, Monograph. Alt. Med. Rev. 1998;3(3):224-226.
Frank M, et al., Hordenine: Pharmacology, Pharmacokinetics and Behavioral Effects in the Horse. Equine Vet. J. 1990;22(6):437-41.
Fraser JG, et al., Child Exposure to Trauma: Comparative Effectiveness of Interventions Addressing Maltreatment. Rockville (MD): Agency for Healthcare Research and Quality (US), Apr. 2013 Comparative Effectiveness Reviews, No. 89.
Gearhardt AN, et al., Neural Correlates of Food Addiction. Archives Gen. Psychiatry 2011;68(8):808-816.
Gearhardt AN, et al., Binge Eating Disorder and Food Addiction. Curr. Drug Abuse Rev. 2011;4(3):201-7.
Gelenberg AJ, et al., Tyrosine for the Treatment of Depression. Am J Psychiatry 1980;137(5):622-623.
Gibson CJ, Alterations in Retinal Tyrosine and Dopamine Levels in Rats Consuming Protein or Tyrosine-Supplemented Diets. J. Neurochemistry, 1988;50(6):1769-1774.

(56) References Cited

OTHER PUBLICATIONS

Galitzky J, et al., Alpha 2-Antagonist Compounds and Lipid Mobilization: Evidence for a Lipid Mobilizing Effect of Oral Yohimbine in Healthy Male Volunteers. Eur. J. Clin. Invest. 1988;18(6):587-94.
Gout B, et al., Satiereal, a Crocus Sativus L Extract, Reduces Snacking and Increases Satiety in a Randomized Placebo-Controlled Study of Mildly Overweight, Healthy Women. Nutr. Res. May 2010;30(5):305-13.
Greeno CG, Wing RR. Stress-Induced Eating. Psychol. Bull. May 1994;115(3):444-64.
Greenway FL, et al., Effect of a Dietary Herbal Supplement Containing Caffeine and Ephedra on Weight, Metabolic Rate, and Body Composition. Obes Res. 2004;12(7):1152-7.
Grimsby J, et al., Increased Stress Response and Beta-Phenylethylamine in MAOB-Deficient Mice. Nat. Genet. 1997;17(2)206-10.
Guilleminault C, et al., Effects of 5-Hydroxytryptophan on Sleep of a Patient With a Brain-Stem Lesion. Electroencephalogr. Clin. Neurophysiol 1973;34:177-184.
Guilleminault C, et al., HVA and 5HIAA CSF Measurements and 5HTP Trials in Some Patients With Involuntary Movements. J Neurol Sci 1973;18(4):435-441.
Haller CA, et al., Enhanced Stimulant and Metabolic Effects of Ephedrine and Caffeine. Clin Pharmacol Ther. 2004;75(4):259-73.
Haller CA, et al., Hemodynamic Effects of Ephedra-Free Weight-Loss Supplements in Humans. Am. J. Med. 2005;118(9):998-1003.
Haslam DW, James WP. Obesity. Lancet Oct. 1, 2005;366(9492):1197-209.
Heck CI, de Mejia EG, Yerba Mate Tea (Ilex paraguariensis): A Comprehensive Review on Chemistry, Health Implications, and Technological Considerations. J. Food Sci. 2007;72(9):R138-51.
Higashiyama A, et al., Effects of L-Theanine on Attention and Reaction Time Response. Journal of Functional Foods, 2011;3(3):171-8.
Hoeger WW, et al., Four-Week Supplementation With a Natural Dietary Compound Produces Favorable Changes in Body Composition. Adv Ther. Sep.-Oct. 1998; 15(5):305-14.
Hoffman JR, et al., Nutritional Supplementation and Anabolic Steroid Use in Adolescents. Medicine & Science in Sports & Exercise 2008;40(1):15-24.
Hoffman JR, et al., Thermogenic Effect of an Acute Ingestion of a Weight Loss Supplement. J. Int. Soc. Sports Nutr. 2009;6:1.
Hoffman JR, et al., Thermogenic Effect from Nutritionally Enriched Coffee Consumption. J. Int. Soc. Sports Nutr. 2006;3:35-41.
Hossain M, et al., β-Phenylethylamine Requires the Dopamine Transporter to Increase Extracellular Dopamine in Caenorhabditis Elegans Dopaminergic Neurons. Neurochem. Int. 2014;73:27-31.
Hung SK, et al., The Effectiveness and Efficacy of Rhodiola Rosea L.: A Systematic Review of Randomized Clinical Trials. Phytomedicine. Feb. 15, 2011;18(4):235-44.
Ito K, et al., Effects of L-Theanine on the Release of Alpha-Brain Waves in Human Volunteers. Nippon Nogeikagaku Kaishi 1998;72:153-157, submitted online by Natural Solutions on Dec. 14, 2002, http://naturalsolutionsradio.com/blog/natural-solutions-radio/effects-l-theanine-release-alpha-brain-waves-human-volunteers.
Johnson PM, Kenny PJ, Dopamine D2 Receptors in Addiction-Like Reward Dysfunction and Compulsive Eating in Obese Rats. Nat. Neurosci. May 2010;13(5):635-41.
Jongkees BJ, et al., Effect of Tyrosine Supplementation on Clinical and Healthy Populations Under Stress or Cognitive Demands—A Review. J. Psych. Res. 2015;70:50-57.
Juneja LR, et al., L-Theanine—A Unique Amino Acid of Green Tea and Its Relaxation Effect in Humans. Trends in Food Science & Technology 1999;10:199-204.
Kakuda T, et al., Inhibiting Effects of Theanine on Caffeine Stimulation Evaluated by EEG in the Rat. Biosci. Biotechnol. Biochem. 2000;64(2):287-293.
Kennedy DO, et al., Herbal Extracts and Phytochemicals: Plant Secondary Metabolites and the Enhancement of Human Brain Function. Adv. Nutr. 2011;2(1):32-50.
Kolar, D, et al., Treatment of Adults with Attention-Deficit/Hyperactiviy Disorder. Neuropsychiatr. Dis. Treat. 2008;4(2):389-403.
Lafontan M, et al., Alpha-2 Adrenoceptors in Lipolysis: Alpha 2 Antagonists and Lipid-Mobilizing Strategies. Am. J. Clin. Nutr. 1992;55(1 Suppl):219S-227S.
Laitinen J, et al., Body Mass Index and Weight Change from Adolescence into Adulthood, Waist-to-Hip Ratio and Perceived Work Ability Among Young Adults. Int. J. Obes. 2005;29(6):697-702.
Loeb C, et al., Levodopa and Huntington's Chorea. J. Neurol. Neurosurg. Psychiatry 1976;39(10):958-61.
Lukaski HC, et al., Chromium Supplementation and Resistance Training: Effects on Body Composition, Strength, and Trace Elements of Men. Am. J. Clin. Nutr. 1996;63(6):954-965.
Magni LR, et al., Fluoxetine Versus Other Types of Pharmacotherapy for Depression. Cochrane Database Syst Rev. Jul. 17, 2013; 7:CD004185.
Manson JE, et al., Body Weight and Mortality Among Women. N. Engl. J. Med. 1995;333(11):677-85.
Mariani JJ, et al., Psychostimulant Treatment of Cocaine Dependence. Psychiatr. Clin. North Am. 2012;35(2):425-39.
Marsden CD, et al., Assessment of Extrapyramidal Disorders. Br. J. Clin. Pharmacol. 1981;11(2):129-51.
Martin J, et al., Chromium Picolinate Supplementation Attenuates Body Weight Gain and Increases Insulin Sensitivity in Subjects with Type 2 Diabetes. Diabetes Care 2006;29:1826-1832.
McManus K (Ed), The Harvard Medical School 6-Week Plan for Health Eating, a Harvard Medical School Special Health Report. Harvard Medical School, 2012, 49 pages.
McNair DM, Lorr M, Droppleman LF, Edits manual: Profile of Mood States. Educational and Industrial Testing Services, 1971, San Diego, CA.
Mir JI, et al., Relative Expression of CsZCD Gene and Apocarotenoid Biosynthesis During Stigma Development in Crocus Sativus L. Physiol. Mol. Biol. Plants, 2012;18(4):371-5.
Misaizu A, et al., The Combined Effect of Caffeine and Ornithine on the Mood of Healthy Office Workers. Prev. Nutr. Food Sci. 2014;19(4):367-72.
Mitchell M, et al., Effect of L-Tryptophan and Phenylalanine on Burning Pain Threshold. Phys. Ther. 1987;37(2):203-5.
Monteiro CA, et al., A New Classification of Foods Based on the Extent and Purpose of Their Processing. Cad Saude Publica. 2010;26(11):2039-2049.
Mouret J, et al., L-Tyrosine Cures, Immediate and Long Term, Dopamine-Dependent Depressions. Clinical and Polygraphic Studies. C R Acad Sci III. 1988;306(3):93-8.
Nakamura M, et al., Characterization of Beta-Phenylethylamine-Induced Monamine Release in Rat Nucleus Accumbens: a Microdialysis Study. Eur. J. Pharmacol. 1998;349(2-3):163-169.
Neri DF, et al., The Effects of Tyrosine on Cognitive Performance During Extended Wakefulness, Aviat. Space Environ. Med. 1995;66:313-319.
NuLivScience, Product Information and Research, available at: http://mediventuresllc.com/images/NuLiv_Science_Brochure.pdf, 32 pgs, 2013.
Okumura Y, et al., Adiposity Suppression Effect in Mice Due to Black Pepper and its Main Pungent Component, Piperine. Biosci. Biotechnol. Biochem. 2010;74(8):1545-9.
Onakpoya I, et al., Chromium Supplementation in Overweight and Obesity: A Systematic Review and Meta-Analysis of Randomized Clinical Trials. Obes. Rev. Jun. 2013;14(6):496-507.
O'Rourke DA, et al., Aberrant Snacking Patterns and Eating Disorders in Patients With Obsessive Compulsive Disorder. J Clin Psychiatry. Oct. 1994;55(10):445-7.
Owen GN, et al., The Combined Effects of L-Theanine and Caffeine on Cognitive Performance and Mood. Nutr. Neurosci. 2008;11(4):193-8.
Pang J, et al., Ilex Paraguariensis Extract Ameliorates Obesity Induced by High-Fat Diet: Potential Role of AMPK in the Visceral Adipose Tissue. Arch. Biochem. Biophys. 2008;476(2):178-85.

(56) References Cited

OTHER PUBLICATIONS

Park, UH, et al., Piperine, a Component of Black Pepper, Inhibits Adipogenesis by Antagonizing PPARγ Activity in 3T3-L1 Cells. J. Agric. Food Chem. 2012;60(15):3853-3860.

Paterson IA, The Potentiation of Cortical Neuron Responses to Noradrenaline by 2-Phenylethylamine Is Independent of Endogenous Noradrenaline. Neurochem. Res. 1993;18(12):1329-36.

Paterson IA, 2-Phenlethylamine: A Modulator of Catecholamine Transmission in the Mammalian Central Nervous System? J. Neurochem. 1990;55(6):1827-37.

Pecoraro N, et al., Chronic Stress Promotes Palatable Feeding, Which Reduces Signs of Stress: Feedforward and Feedback Effects of Chronic Stress. Endocrinology, Aug. 2004;145(8):3754-62.

Pedram P, et al., Food Addiction: Its Prevalence and Significant Association with Obesity in the General Population. PLoS One, 2013;8(9):e74832.

Petkov VD, et al., Effects of Alcohol Aqueous Extract From Rhodiola Rosea L. Roots on Learning and Memory. Acta Physiol. Pharmacol. Bulg. 1986;12:3-16.

Pike KM, et al., Antecedent Life Events of Binge-Eating Disorder. Psychiatry Res. 2006;142(1):19-29.

Pittler MH, Ernst E, Dietary Supplements for Body-Weight Reduction: A Systematic Review. Am. J. Clin. Nutr. 2004;79:529-36.

Pohle-Krauza RJ, et al., Dietary Restraint and Menstrual Cycle Phase Modulated L-Phenylalanine-Induced Satiety. Physiol. Behav. Mar. 18, 2008;93(4-5):851-61.

Poldinger W, et al., A Functional-Dimensional Approach to Depression: Serotonin Deficiency as a Target Syndrome in a Comparison of 5-Hydroxytryptophan and Fluvoxamine. Psychopathology 1991;24(2):53-81.

Polivy J, Herman CP, Distress and Eating: Why Do Dieters Overeat? Int. J. Eat. Disord. Sep. 1999;26(2):153-64.

Portas CM, et al., Serotonin and the Sleep/Wake Cycle: Special Emphasis on Microdialysis Studies. Prog. Neurobiol. Jan. 2000;60(1):13-35.

Poulain M, et al., The Effect of Obesity on Chronic Respiratory Diseases: Pathophysiology and Therapeutic Strategies. CMAJ. Apr. 25, 2006;174(9):1293-9.

Rattue P, Seeing Fatty Food Pictures Encourages Impulse Eating. Medical News Today, 2012, http://www.medicalnewstoday.com/articles/247283.php.

Rezaee R, Hosseinzadeh H, Safranal: From an Aromatic Natural Product to a Rewarding Pharmacological Agent. Iran J. Basic Med. Sci. 2013;16(1):12-26.

Rhodiola rosea, Monograph. Alt. Med. Review, 2002;7(5):421-423.

Roberts AT, et al., The Effect of an Herbal Supplement Containing Black Tea and Caffeine on Metabolic Parameters in Humans. Alternative Medicine Review 2005;10(4):321-325.

Rodel W, Petrzika M, Analysis of the Volatile Components of Saffron. J. High Resolution Chromotogr. 1991;14(11):771-774.

Sabelli H, et al., Phenylethylamine and Brain Function. Biochem. Pharmacol. 1978;27(13):1707-11.

Sabelli H, et al., Sustained Antidepressant Effect of PEA Replacement. J. Neuropsychiatry Clin. Neurosci. 1996;8(2):168-71.

Sadzuka Y, et al., The Effects of Theanine, as a Novel Biochemical Modulator, on the Antitumor Activity of Adriamycin. Cancer Lett. 1996;105(2):203-209.

Schulte EM, et al., Which Foods May Be Addictive? The Roles of Processing, Fat Content, and Glycemic Load. PLoS One 2015;10(2):e0117959.

Slezak T, et al., Determination of Synephrine in Weight-Loss Products Using High Performance Liquid Chromatography with Acidic Potassium Permanganate Chemiluminescence Detection. Anal. Chim. Acta, 2007;593(1):98-102.

Srinivasan K, Black Pepper and its Pungent Principle-Piperine: A Review of Diverse Physiological Effects. Crit. Rev. Food Sci. Nutr. 2007;47(8):735-48.

Strasser F, et al., Safety, Tolerability and Pharmacokinetics of Intravenous Ghrelin for Cancer-Related Anorexia/Cachexia: A Randomised, Placebo-Controlled, Double-Blind, Double-Crossover Study. Br. J. Cancer 2008;98(2):300-8.

Sugiyama T, Sadzuka Y, Combination of Theanine With Doxorubicin Inhibits Hepatic Metastasis of M5076 Ovarian Sarcoma. Clin. Cancer Res. 1999;5:413-416.

Sved AF, et al., Tyrosine Administration Reduces Blood Pressure and Enhances Brain Norepinephrine Release in Spontaneously Hypertensive Rats. Proc. Natl. Acad. Sci. USA 1979;76(7):3511-4.

Szabo A, et al., Phenylethylamine, a Possible Link to the Antidepressant Effects of Exercise? Br. J. Sports Med. 2001;35(5):342-3.

Taheri S. The Link Between Short Sleep Duration and Obesity: We Should Recommend More Sleep to Prevent Obesity. Arch. Dis. Child 2006;91:881-884.

Tanaka H, et al., Health Status and Lifestyle Factors as Predictors of Depression in Middle-Aged and Elderly Japanese Adults: A Seven-Year Follow-Up of the Komo-Ise Cohort Study. BMC Psychiatry 2011;11:20.

Ter Borg PC, et al., The Relation Between Plasma Tyrosine Concentration and Fatigue in Primary Biliary Cirrhosis and Primary Sclerosing Cholangitis. BMC Gastroenterol. 2005;5:11.

Tomiyama A, et al., Comfort Food is Comforting to Those Most Stressed: Evidence of the Chronic Stress Response Network in High Stress Women. Psychoneuroendocrinology 2011;36(10):1513-9.

Udo T, et al., Modeling the Effects of Positive and Negative Mood on the Ability to Resist Eating in Obese and Non-Obese Individuals. Eat Behav. 2013;14(1):40-46.

U.S. Department of Agriculture, et al., Dietary Guidelines for Americans. 2010, www.dietaryguidelines.gov, 112 pages.

Vaagenes H, et al. Methylated Eicosapentaenoic Acid and Tetradecylthioacetic Acid: Effects on Fatty Acid Metabolism. Biochem. Pharmacol. 1999;58(7):1133-43.

Vandati H, et al., Antideppressant Effects of Crocin and its Effects on Transcript and Protein Levels of CREB, BDNF, and VGF in Rat Hippocampus. Daru 2014;22(1):16.

Van Praag HM, et al., Therapeutic Indications for Serotonin-Potentiating Compounds: A Hypothesis. Biol. Psychiatry 1987;22(2):205-212.

Vladeva SV, et al., Effect of Chromium on the Insulin Resistance in Patients With Type II Diabetes Mellitus. Folia Med (Plovdiv) 2005;47(3-4):59-62.

Vukovich MD, et al., Caffeine-Herbal Ephedra Combination Increases Resting Energy Expenditure, Heart Rate and Blood Pressure. Clin. Exp. Pharmacol. Physiol. 2005;32(1-2):47-53.

Wadden TA, et al., Efficacy of Lifestyle Modification for Long-Term Weight Control. Obes. Res. 2004;12 Suppl:151S-162S.

Wang Y, et al., Will All Americans Become Overweight or Obese? Estimating the Progression and Cost of the U.S. Obesity Epidemic. Obesity 2008;16(10):2323-2330.

Warne JP, Shaping the Stress Response: Interplay of Palatable Food Choices, Glucocorticoids, Insulin and Abdominal Obesity, Mol. Cell Endocrinol. Mar. 5, 2009;300(1-2):137-46.

Westerterp-Plantenga MS, et al., Body Weight Loss and Weight Maintenance in Relation to Habitual Caffeine Intake and Green Tea Supplementation. Obes. Res. Jul. 2005 ;13(7):1195-204.

Wood DR, et al. Treatment of Attention Deficit Disorder with DL-Phenylalanine. Psychiatry Res. 1985;16(1):21-26.

Wurtman RJ, Wurtman JJ, Brain Serotonin, Carbohydrate-Craving, Obesity and Depression. Obes. Res. Nov. 1995 ;3(Suppl 4):477S-480S.

Wyatt RJ, et al., Effects of 5-Hydroxytryptophan on the Sleep of Normal Human Subjects. Electroencephalogr. Clin. Neurophysiol. 1971;30(6):505-509.

Yokogoshi H, et al., Effect of Theanine, R-Glutamylethylamide, on Brain Monoamines and Striatal Dopamine Release in Conscious Rats. Neurochem. Res. 1998;23(5):667-673.

Young SN, How to Increase Serotonin in the Human Brain Without Drugs. Rev. Psychiatry Neurosci. 2007;32(6):394-99.

Zhou BH, et al., Antidepressant-Like Activity of the Gastrodia Elata Ethanol Extract in Mice. Fitoterapia Dec. 2006; 77(7-8):592-4.

Ziaee T, et al., Saffron Reduced Toxic Effects of its Constituent, Safranal, in Acute and Subacute Toxicities in Rats. Jundishapur J. Nat. Pharm. Prod. 2014;9(1):3-8.

(56) References Cited

OTHER PUBLICATIONS

Notification of Transmittal of the International Search Report and the Written Opinion of the International Searching Authority, including International Search Report, and Written Opinion of the International Searching Authority, for International Application No. PCT/US2016/051796, dated Dec. 12, 2016 (12 pages).

Cooper, K., Dosages of *Rhodiola rosea*, available at: http://www.livestrong.com/article/517874-side-effects-for-long-time-usage-of-ashwagandha/ updated Aug. 16, 2013, retrieved Oct. 25, 2015 (2 pages).

Notification concerning transmittal of International Preliminary Report on Patentability, and International Preliminary Report on Patentability, for International Application No. PCT/US2016/051796, dated Mar. 29, 2018, 10 pages.

* cited by examiner

COMPOSITIONS FOR REGULATION AND CONTROL OF APPETITE

CROSS REFERENCE TO RELATED APPLICATIONS

None

FIELD OF THE INVENTION

The invention describes novel compositions for regulation and/or control of appetite, said compositions providing a whole body approach for management of weight. Said compositions comprise a combination of components with unexpected synergistic activity and/or beneficial effects when consumed.

BACKGROUND

To date, medicines for control and/or reduction of weight generally involve one active agent that has a limited or singular biologic target. For example, one existing composition on the market is tetrahydrolipstatin ((S)—((S)-1-((2S, 3S)-3-hexyl-4-oxooxetan-2-yl)tridecan-2-yl) 2-formamido-4-methylpentanoate, which biologically targets pancreatic lipases, acting as an inhibitor of these lipases. Another treatment marketed for weight control is phentermine or phenyl-tertiary-butylamine, a sympathomimetic amine that primarily targets trace amine-associated receptor 1 (TAAR1), thereby acting as an activator of TAAR1, with some possible activity on vesicular monoamine transporter 2 (VMAT2). Lorcaserin HCl or (1R)-8-chloro-1-methyl-2,3,4,5-tetrahydro-1H-3-benzazepine is still another treatment identified for weight reduction, and has a singular activity, acting as a selective $5\text{-HT}_{2c}$ (serotonin 2C) receptor agonist. These marketed products each have essentially a singular biologic target, offering limited flexibility to the person taking the product and can provide safety issues to certain persons, especially when taken in higher doses. There remains a need for more effective compositions for weight management, including ones that control and regulate appetite more effectively with fewer side effects.

Because the mechanisms of appetite regulation are multi-faceted, there remains a need for a multi-faceted approach to appetite control and weight management. These and other needs are met by the compositions described below.

OVERVIEW

Described herein are novel compositions and uses for said novel compositions for appetite regulation and weight management. The described compositions overcome one or more of the above described problems or obstacles. For example, the compositions described herein offer a multi-targeted approach by combining a plurality of components that together target a plurality of systems in the body at one time. The compositions described herein being multi-targeted provide the plurality effects on many biologic systems in the body to help promote weight reduction and appetite regulation, such as the neurologic system, the endocrine system, the cardiovascular system, the urinary system, the gastrointestinal system. Furthermore, with the compositions described herein, cellular metabolism and thermogenesis are enhanced. In addition, the compositions described herein help manage eating behaviors and stress, such as lessening uncontrolled cravings and reducing mental anxiety, both of which have more recently been found to be reasons that weight loss is either not obtained or the loss is not maintained. In the compositions described herein, many of the components are utilized in much lower doses than are typically used by others or than have been used when said independent component was tested for its effectiveness. The overall effect of the compositions described herein is greater than would be expected based on the independent performance of each component described herein and when said independent components are provided at the doses described herein.

The compositions described herein provide a unique combination of components with a multi-targeted approach, so that the combination when taken by a person, will biologically energize the brain, the endocrine system, the stomach, and the heart and cardiovascular system, while reducing stress, anxiety, controlling desire and reward centers (e.g., satiation), and promoting cellular metabolism, maintaining or regulating blood sugar dynamics and increasing thermogenesis. The compositions described herein provide a unique combination of components that manage negative effects associated with obesity (e.g., stress, anxiety, sleeplessness, pain, low energy) while increasing cellular metabolism, regulating blood sugar and increasing thermogenesis when taken near the time of eating a meal.

In one or more embodiments, the compositions described herein include a unique and unexpected combination of botanical substances (e.g., plants, plant substances, and/or plant extracts), amino acids (and/or amino acid precursors), and one or more metals. The components in or extracted from the botanical substances described herein are considered natural or derived from natural components. At least some of the botanical substances included with the compositions described herein are provided as components not generally provided in a traditional and/or Western diet. Most of the botanical substances are included in amounts that exceed the amount that would be found if that botanical substance were included in a person's diet. Thus, while some or many of the components described herein may be naturally occurring or found in food, they could not be consumed in the amounts described herein and would not be consumed in the combination described herein.

The botanical substances include a plurality of components that in combination offer more than a singular target and instead not only influence and target neurotransmitters, the combination of botanical substances also increase resistance to stress, enhance cellular performance, improve sleep, reduces fatigue, enhance mental performance, increase absorption of amino acids, increase thermogenesis and metabolism, and influence eating and behavior toward eating (facilitates reward and satiation), to name a few of the effects when the botanical substances (or their extracts and/or active components) are combined in the unique compositions described herein. Together, the combination of botanical substances as described herein are provided in a blend that has not been previously found or reported to be effective for weight loss. When combined as described herein, many, if not most or all of the botanical substances of the compositions described herein are provided at a dose that higher or much higher than were that botanical substance to be consumed naturally in food, yet are also lower or significantly lower than were that botanical substance to be provided on its own, such as at a clinically recommended dose found to be clinically effective when used on its own. Because said botanical substance doses remain lower or significantly lower that when provided in a clinical setting to be clinically effective, the compositions described herein are not associated with side effects found in many of the alternative treatments or medicines used singularly and clinically to control weight.

The botanical substances include but are not limited to crocus (*Crocus sativus*), *Rhodiola rosea*, *Astragalus membranaceus*, *Panax notoginseng*, and black peppercorns. Generally, many if not all of these botanical substances (or their extracts and/or active components) are provided in the compositions described herein.

The *crocus* when used as described herein may be provided as an extract that generally includes at least one or more of an active component, crocin, which is a dopamine reuptake inhibitor, and/or another active component, safranal, a serotonin reuptake inhibitor. The *crocus* extract (and/or active components thereof) are effective at regulating the neurotransmitters, dopamine and serotonin. When the *crocus* extract having both crocin and safranal are provided in the compositions described herein and in the doses described, the *crocus* extract is included to reduce snacking and/or frequency of snacking, increase satiation between meals and, to provide a component to the composition described herein that helps regulate appetite between meals, thereby providing at least one facet of weight management in an overall multi-faceted strategy as described herein. When the *crocus* extract having both crocin and safranal are provided in the compositions described herein and in the doses described, the dual neurotransmitter effects are introduced at doses of the *crocus* extract that is less than found when said extract is used alone (clinically) to provide clinical effects. The *crocus* extract may also be modified to alter one of both amounts of the neurotransmitters, thereby enhancing or reducing the dopamine and/or serotonin regulation. The *crocus* extract is also included to reduce anxiety and/or symptoms associated with depression (without increasing appetite), thereby providing another facet in a converging pathway towards weight management for the overall multi-faceted strategy as described herein.

The *Rhodiola rosea* when used as described herein may be provided as an extract that is effective at lowering cortisol, and enhancing serotonin production. When the extract of *Rhodiola rosea* is provided in the compositions described herein and in the doses described, the *Rhodiola rosea* extract is included to reduce stress, eliminate fatigue, to reduce symptoms of depression, and improve cellular function and oxidation/energetics, and stamina and endurance in persons experiencing or having experienced physical stress and/or mental stress, including anxiety and/or depression. In some embodiments, the *Rhodiola rosea* extract is provided in the compositions described herein and in a dose described herein that is less than found when said extract is used alone (clinically) to provide clinical effects. The extract of *Rhodiola rosea* provides a component to the composition described herein that helps cellular performance and mental performance of a person, thereby providing additional facets and/or converging pathways towards weight management in the overall multi-faceted strategy described herein.

The *Astragalus membranaceus* when used as described herein may be provided as an extract of the root that is effective as an adaptogen, protecting against stress (physical or mental), reducing symptoms of stress as well as improving cellular function during stress and protecting the immune system, as well as lowering blood pressure, lowering cholesterol and acting as an antioxidant and a mild diuretic. When the root extract of *Astragalus membranaceus* is provided in the compositions described herein and in the doses described, the *Astragalus membranaceus* root extract is included to reduce stress, to reduce symptoms of stress, improve cellular function and oxidation/energetics, and improving heart function. In some embodiments, the *Astragalus membranaceus* root extract is provided in the compositions described herein and in a dose described herein that is less than found when said extract is used alone (clinically) to provide clinical effects. The *Astragalus membranaceus* root extract provides a component to the composition described herein that helps cellular performance, positively effects heart and kidney function and mental performance in a person, thereby providing additional facets and/or converging pathways towards weight management in the multi-faceted strategy described herein.

*Panax notoginseng* when used as described herein may be provided as an extract of the root that is effective as an adaptogen; it effects function of the adrenal glands, protects against stress (physical or mental), reduces symptoms of stress or pain as well as improving cellular function during stress, protects the immune system, normalizing blood pressure, lowers cholesterol and reduces swelling. When the root extract of *Panax notoginseng* is provided in the compositions described herein and in the doses described, the *Panax notoginseng* root extract is included to reduce stress, to reduce symptoms of stress, improve cellular function and oxidation/energetics, and improving heart function. The *Panax notoginseng* root extract provides a component to the composition described herein that helps cellular performance, effects heart and kidney function, and mental performance of a person, thereby providing additional facets and/or converging pathways towards weight management in the multi-faceted strategy described herein. In some embodiments, the *Panax notoginseng* root extract is provided in the compositions described herein and in a dose described herein that is less than found when said extract is used alone (clinically) to provide clinical effects. In combination, root extracts of *Astragalus membranaceus* and *Panax notoginseng* when provided together improved vitamin, amino acid, protein and mineral absorption, and improve cellular metabolism by enhancing adenosine triphosphate (ATP) production.

Black pepper fruit or peppercorns (from *Piper nigrum* and/or *Piper longum*) when used as described herein may be provided as an extract of the peppercorns (e.g., including peperine) that is effective at improving uptake of nutrients, promotes urination, acting as an antioxidant, stimulating fat cells (breakdown of fat cells), and increasing rate of metabolism. In some embodiments, the black pepper extract is provided in the compositions described herein and in a dose described herein that is less than found when said extract is used alone (clinically) to provide clinical effects. When the black pepper extract is provided in the compositions described herein and in the doses described, the black pepper extract is included to improve and increase metabolism, increase thermogenesis, increase nutrient uptake, and reduce fat cells, thereby providing additional facets and/or converging pathways towards weight management in the overall multi-faceted strategy described herein.

When several of the botanical substances are combined, unexpected synergistic effects were found. For example, *Rhodiola rosea* extract and black pepper extract (e.g., peperine) are believed to provide synergistic benefits in improving mental function, reducing anxiety and/or alleviating symptoms of depression. Said synergy is, in part, how said doses may be lower or much lower than when said botanicals are used independently and for said clinical effectiveness.

Simply including the botanical substances described above in a composition described herein provides a multifaceted approach to appetite regulation, and control of cravings, by targeting a plurality of organ systems, including the brain and various neurological pathways, the cardiovascular system, the endocrine system, the gastrointestinal system, the musculoskeletal system, the urinary system, as well as providing improvements in cellular metabolism and cellular uptake of nutrients.

The compositions described herein further comprise a plurality of amino acids or precursors or related primary amines thereof that even further influence the control and regulation of appetite. These amino acids are also a unique blend that include but are not limited to some or all of the following: tyrosine or acetyl L-tyrosine, phenylalanine, theanine, hydroxytryptophan (5-HTP), and phenylethylamine.

Tyrosine, generally as acetyl L-tyrosine, a precursor of dopamine, norepinephrine, and epinephrine (by way of L-DOPA), is provided in the compositions described herein and is often provided in an isolated form suitable for consumption. It may be provided as L acetyl L-tyrosine or some variation thereof used to produce dopamine or norepinephrine. It maintains or can elevate neurotransmitter levels, and is considered to help reduce stress-induced memory deficits, symptoms of stress, and to improve memory, and reduce mental and physical stress. When tyrosine is provided in the compositions described herein and in the doses described, the tyrosine is included to improve appetite regulation, reduce hunger, and elevate performance when under stress, thereby providing additional facets that intersect and/or merge with the botanical substances, to provide a more balanced approach to weight management in the overall multi-faceted strategy described herein.

Phenylalanine, when provided as L-phenylalanine is an essential amino acids, which is a precursor for tyrosine, hence for dopamine, norepinephrine, and epinephrine. It is provided in the compositions described herein and often in an isolated form suitable for consumption. Phenylalanine may be provided in the form of DL phenylalanine which includes a more rapidly absorbed form (D-phenylalanine) along with L-phenylalanine. Phenylalanine or DL phenylalanine has antidepressant effects, and helps maintain or promote neurotransmitter levels, and is considered to help reduce symptoms of stress or depression, to suppress appetite (by stimulating cholecystokinin), accelerate weight loss and improve overall body composition (increase lean mass versus fat mass), and may reduce long-term pain. When phenylalanine or DL phenylalanine is provided in the compositions described herein and in the doses described, it is included to help suppress appetite, improve weight loss, and reduce symptoms that may be associated with depression, thereby providing additional facets that intersect and/or merge with the botanical substances, to provide a more balanced approach to weight management in the overall multi-faceted strategy described herein.

Theanine, an amino acid analogue or derivative of glutamine, is provided in the compositions described herein and is generally provided in an isolated form suitable for consumption. It may be provided as L-theanine or some variation thereof that increases dopamine and likely serotonin availability and/or production, and also increases GABA and glycine levels in the brain. It is considered to help stabilize and/or elevate mood and to ease symptoms of anxiety, to improve memory and/or mental performance, and reduce mental and physical stress. Theanine may also balance or reduce the stimulatory effects associated with caffeine (e.g., may reduce caffeine-associated nervousness). When theanine is provided in the compositions described herein and in the doses described, the theanine is included to improve regulation of appetite, to reduce stress and/or nervousness, and improve memory and mental performance, thereby providing additional facets that intersect and/or merge with the botanical substances, to provide a more balanced approach to weight management in the overall multi-faceted strategy described herein.

Hydroxytryptophan is an amino acid and a precursor in the production of serotonin and melatonin. It is often provided in an isolated form suitable for consumption. It has been provided for alleviating symptoms associated with depression. It is also included to aid in serotonin production, which is lower in people considered obese, and may increase feelings of fullness. When hydroxytryptophan is provided in the compositions described herein and in the doses described, the hydroxytryptophan is included to improve in regulating appetite, mood and sleep, thereby providing additional facets that intersect and/or merge with the botanical substances, to provide a more balanced approach to weight management in the overall multi-faceted strategy described herein.

Phenylethylamine is a primary amine produced from L-phenylalanine and stimulates the release of dopamine and norepinephrine from neurons, and may also stimulate acetylcholine release from neurons. It is often provided in an isolated form suitable for consumption. It has been provided for alleviating symptoms associated with depression. It may also mitigate addictive behaviors (e.g., behave like a natural amphetamine), and may aid in lipolysis, or degradation of lipids or fat. When phenylethylamine is provided in the compositions described herein and in the doses described, the phenylethylamine is included to improve in regulating appetite, mood and increase cell or fat metabolism, thereby providing additional facets that intersect and/or merge with the botanical substances, to provide a more balanced approach to weight management in the overall multi-faceted strategy described herein.

Combining some or all the botanical substances described above with some or all the amino acids (or related precursors or amines) in a composition described herein provides an even more multi-faceted composition, with one or more converging pathways, that together, in any of the described combinations (and compositions described herein) promote appetite regulation, fat metabolism, as well as improve cellular metabolism and cellular update of nutrients, while also providing components or precursors that help to control hunger and cravings, as well as control mood and/or depression, which is often associated with persons trying to lose or manage their weight. The unexpected combination of components described herein may in fact behave synergistically, such that the synergism enhances many of the independent effects, thereby with the compositions described herein, there is believed to be synergistic improvement in amino acid absorption, cellular metabolism, and/or mood regulation and/or control of hunger and cravings when the botanical substances such as the *crocus* extract (or one or more of its effective components), the extract of *Rhodiola rosea* (or one or more of its effective components), the extract of *Astragalus membranaceus* (or one or more of its effective components), and/or the extract of (or one or more of its effective components) *Panax notoginseng*) are provided in combination with any of the amino acid combinations described herein.

The compositions described herein may further comprise one or more metals that include but are not limited to transition metals (e.g., chromium) and alkaline earth metals (e.g., calcium). Said metals are provided in suitable valences to prevent toxicity. For example, chromium is provided as trivalent chromium (e.g., chromium (III) nicotinate, chromium polynicotinate). It may also be provided in other forms suitable for consumption. Chromium is provided to modulate insulin or improve the blood sugar balance, and is provided to decrease appetite, decrease body fat, and reduce cravings for food that contain high levels of fat. Chromium can also improve cellular performance, increase energy and may reduce symptom associated with depression. When chromium is provided in the compositions described herein and in the doses described, the phenylethylamine is included to decrease in appetite, increase reduction in body fat without reducing lean body mass, increase cell or fat metabolism and reduce cravings, thereby providing additional facets that intersect and/or merge with the botanical substances and amino acids described above, to provide a more balanced approach to weight management in the overall multi-faceted strategy described herein.

The compositions described herein may further comprise one or more vitamins, vitamin alternatives, nicotinamide riboside (a B-3 vitamin) or effective nicotinamide adenine dinucleotide (NAD) precursors, a stilbenoid compound, its analogs or derivatives, and/or caffeine. Caffeine is provided, for example, to increase thermogenesis, improve energy, and improve cellular oxidation. One or more stilbenoid compounds may be provided, for example, to improve cognition and/or enhance bioabsorption of accompanying components or to improve mitochondrial function. Nicotinamide riboside or an effective NAD precursor is provided, for example, to improve metabolism by enhancing NAD levels and/or production of NAD or to enhance mitochondrial function and has been associated with improvements in cellular energy, cellular repair, as well as improving mental well-being, and sleep and wakefulness. Vitamins may be provided, for example, to supplement the nutritional needs of the person and promote good health. Deficiency of certain vitamins, such as the B vitamins, can contribute to unhealthy weight gain. Thus, vitamins, when included, may, for example, be provided as all or some of the B vitamins, such as vitamin B-12 and/or vitamin B-6 and/or vitamin B-3. Additional vitamins may also be included as desired.

The compositions described herein are, in one or more forms, provided with a combination of components described above that together target a plurality of anatomic systems, neurologic pathways, and metabolic pathways in order to increase cellular metabolism while positively influence eating behavior, controlling hunger, removing addictive eating patterns and reducing cravings. The unique combination of components addresses the numerous pathways and anatomic systems to influence the behavior of eating while also stimulating cells to metabolize, to reduce fat storage while maintaining blood sugar levels and various important and/or essential amino acids.

The compositions described herein may include all the components together (e.g., in a single formulation). The composition may comprise several components provided concomitantly. Providing concomitantly may include providing together, such as in a blend, or mixture. Providing concomitantly may include providing simultaneously, or concurrently, or providing in parallel, such as at or about a same time or at or about a same dosing schedule. In one or more embodiments, the composition may comprise several components provided independently. The composition may comprise several components provided sequentially.

The compositions described herein may further comprise one or more excipients, including but not limited to filler, disintegrant, glidant, flavorant, colorant, sweetener, and/or natural preservative. The compositions with the one or more optional excipients may be provided in dry form and in a liquid form.

Thus, in one or more embodiments, the compositions when fully formulated may be absorbed at least in part by the oral mucosa and/or by the stomach after administration or delivery. The compositions when fully formulated may be provided for oral delivery. The forms for oral delivery may include but are not limited to tablet, capsule, liquid, powder, resinate, waxate, losenge, wafer, gummy, gel, gum.

The compositions described herein, including any excipients, will be those Generally Recognized as Safe (GRAS) in accordance with the Federal Food, Drug and Cosmetic Act. In one or more embodiments, the compositions described herein, including any excipients or fillers, will generally not include products prepared by or produced by genetically modified organisms.

The described compositions that include the described combination are provided to a subject. The described compositions may be provided as a supplement. The described compositions may be provided as a medical food. In some embodiments, the activity and/or effectiveness of the described compositions that include the described combination are far greater than would be predicted for a combination of two or more of the components, thereby behaving synergistically. When said composition is provided to the subject, the composition comprising the described combination of components will include components having a synergistic effect, even when provided in doses that are lower than those doses found effective when used singly or independently. The synergistic effect is considered an activity or effect that is better than the activity or effect of said single component when used alone or separately and/or when used in a higher dose as compared with the dose used with the composition described herein.

For a subject taking a composition described herein, the composition may provide one or more of the following: appetite and/or hunger control, reduced cravings, reduction in addictive eating patterns, reduction in snacking, increased neural transmission to balance mood and reduce anxiety, increased cellular uptake, reduction in mental anxiety and/or depression, increased satiation. Biologically, the compositions described herein may increase release of serotonin and/or dopamine in the body, may reduce reuptake of serotonin and/or dopamine, may enhance amino acid absorption, may inhibit enkephalinase production in the body, may increase metenkephalin in the brain, may reduce cortisol levels, may stimulate lipolysis, may enhance production of cholecystokinin, may improve REM cycle during sleep, and may increase absorption of amino acids by certain cells.

The novel compositions described herein may be provided in therapeutically acceptable amounts or orally effective amounts for controlling or regulating appetite, such as for a subject in need of appetite control or regulation of appetite or reduction of symptoms associated with stress, depression and/or fatigue. The novel compositions may provide increased satiation after eating when said composition is taken before a meal or after a meal. The novel compositions may reduce cravings after eating when said composition is taken before a meal or after a meal. The novel compositions may provide increased energy production after eating. The novel compositions may provide increased serotonin and/or dopamine levels in a subject, such as a subject in need thereof. The novel compositions may enhance amino acid absorption in the subject, such as a subject in need thereof. The novel compositions may help alleviate and/or reduce anxiety, or symptoms associated with anxiety in the subject, such as a subject in need thereof.

In one or more embodiments are described compositions for regulation of appetite. The compositions comprise at least botanical substances, amino acids, and a metal. In some embodiments, the composition further comprises one or more vitamins. In some embodiments, the composition further comprises caffeine. In some embodiments, the botanical substances includes an extract from a root of *Astragalus membranaceus*, an extract from a root of *Panax notoginseng*, an extract from a root of *Rhodiola rosea*, and an extract from a flower of *Crocus Sativus*. In some embodiments, the botanical substances includes an extract from a root of *Astragalus membranaceus*, extract from a root of *Panax notoginseng*, extract from a root of *Rhodiola rosea*, extract from a flower of *Crocus sativus*, and extract from peppercorns. In some embodiments, the composition is provided in a dry form for oral administration. In some embodiments, the composition is provided as a tablet. In some embodiments, the composition is provided as a powder. In some embodiments, the composition further comprises one or more excipients. In some embodiments, the excipients include a soluble fiber, an acid, one or more natural flavors, one or more natural colors, at least one sweetener and silica. In some embodiments, the metal is or includes a form of calcium. In some embodiments, the metal is or includes a form of chromium. In some embodiments, the amino acids are selected from any one or more of natural amino acids, one or more amino acid analog, and one or more amino acid precursor. In some embodiments, the amino acids are acetyl L-tyrosine, phenylalanine, theanine, hydroxytryptophan, and phenylethylamine. In some embodiments, the amino acids comprise up to 55% of the composition based on the weight of the composition. In some embodiments, the amino acids comprise up to 15% of the composition based on the weight of the composition. In some embodiments, the botanical substances comprise up to 15% of the composition based on the weight of the composition. In some embodiments, the botanical substances comprise up to 5% of the composition based on the weight of the composition. In some embodiments, the metal comprises up to 5% of the composition based on the weight of the composition. In some embodiments, the metal comprises up to 0.01% of the composition based on the weight of the composition. In some embodiments, the composition further comprises one or more excipients, the one or more excipients comprising between about 30 wt. % and 35 wt. % of the composition based on the weight of the composition. In some embodiments, the composition further comprises one or more excipients, the one or more excipients comprising between about 75 wt. % and 85 wt. % of the composition based on the weight of the composition.

In one or more embodiments are also described herein a method of use of any of the compositions described herein. The method includes administering an effective amount of a composition. The composition comprises at least botanical substances, amino acids, and a metal. The administering includes providing orally to a subject at least one dose of the composition per day. The administering further comprises providing the composition at least or about 30 minutes or 45 minutes before a meal, or may be at least or about 30 minutes or 45 minutes after a meal. The meal is selected preferably as an afternoon meal, an early evening meal, and an evening meal. The meal may further comprise a morning meal. The administering may comprise providing the composition once per day at least or about 30 minutes or at least or about 45 minutes before the meal. The administering may comprise providing the composition once per day at least or about 30 minutes or at least or about 45 minutes after the meal. The administering may comprise providing the composition twice per day, each administering occurring at least or about 30 minutes or about 45 minutes before the meal or after the meal.

DETAILED DESCRIPTION

Although making and using various embodiments are discussed in detail below, it should be appreciated that as described herein are provided many inventive concepts that may be embodied in a wide variety of contexts. Embodiments discussed herein are merely representative and do not limit the scope of the invention.

The novel compositions described herein include a combination of botanical substances. The botanical substances may be provided as extracts that include the active ingredient(s) in or from each botanical substance. A first botanical substance is a *crocus* extract or an extract from at least *Crocus sativus*. A second botanical substance is an extract from *Rhodiola rosea*. A third botanical substance is an extract from *Astragalus membranaceus*. A fourth botanical substance is an extract from *Panax notoginseng*. A fifth botanical substance is an extract from black pepper.

In one or more embodiments of the composition, the composition includes a combination of at least the first botanical substance, the second botanical substance, the third botanical substance, and the fourth botanical substance. In one or more embodiments of the composition, the composition includes a combination of at least the first botanical substance, the second botanical substance, the third botanical substance, the fourth botanical substance and the fifth botanical substance. It is also contemplated that fewer than all the first to fourth botanical substances or the first to fifth botanical substances may be combined in the compositions described herein. It is contemplated that more than the first botanical substance, the second botanical substance, the third botanical substance, the fourth botanical substance, and/or the fifth botanical substance may be included in compositions described herein. Some or all of the first to fifth botanical substances included with the compositions described herein or at least some combination of these botanical substances are included with the compositions described herein, or their extracts with the one or more active ingredients from said botanical substances. These botanical substances are botanical substances not generally provided in a traditional diet and/or traditional or usual Western diet. Further botanical substances may also be included.

The *crocus* extract or the first botanical substance is also known as or referred to as autumn *crocus* or saffron *crocus* (*Crocus* genus, Iridaceae family). The *crocus* extract may be represented by an extract from the flower of *Crocus sativus*, by saffron or saffron threads, as examples. The *crocus* extract or active ingredients from the *crocus* extract may also be in the form of safranal and/or crocin. The *crocus* extract may be an extract from or the stigma of *Crocus sativus*. The *crocus* extract may be an extract from or the stigma of *Crocus sativus* in which the safranal and/or crocin levels have been selectively modified and the ratio of safranal and crocin is adjusted to effectively modulate their respective neurotransmitters. Modifying crocin levels will affect amounts of glutamate and dopamine. Modifying safranal levels will affect appetite control. The activities and/or effects related to administration of the *crocus* extract and/or active ingredients thereof were described above. The amount of *crocus* extract (or active ingredients thereof) in a single dose of a composition described herein may be from about 1 mg to about 50 mg, or up to about 60 mg, or up to about 70 mg. In some embodiments, the amount of *crocus* extract may be from about 10 mg to about 40 mg, or may be in any range or amount therebetween. A total daily amount of the *crocus* extract (or active ingredients thereof) is often less than 100 mg, or may be less than 90 mg, or may be less than 80 mg, or may be less than 70 mg. In one or more embodiments, the amount of *crocus* extract in a single dose of a composition described herein is less than an amount found to be used in studies with *crocus* extract alone for persons with stress and/or considered overweight, in which said doses were typically about 177 mg per day (from a liquid saffron extract, given in two capsules, each containing about 88 mg). In one or more embodiments, the amount of *crocus* extract provided with a daily dose of a composition described herein is less than an effective amount provided in studies with *crocus* extract when the *crocus* extract was used on its own for a person, such as a person having stress and/or considered overweight.

The extract from *Rhodiola rosea* or the second botanical substance is also referred to as golden root, rose root, Aaron's rod, king's crown (*Rhodiola* genus, Crassulaceae family). The extract is generally represented as an extract from the root of *Rhodiola rosea*. In some embodiments, the extract or active ingredients from the extract include at least many of the following, including rosavin, rosarin, rosin, salidroside, with or without p-tyrosol, rhodioniside, rhodiolin, rosiridin, and additional polyphenols, phenols, terpenoids, flavenoids, anthraquinones, and/or phenocarbonic acids. The activities and/or effects related to administration of the *Rhodiola rosea* extract and/or the active components thereof were described above. The amount of the extract from *Rhodiola rosea* (or its active ingredients) in a single dose of a composition described herein may be from about 50 mg to about 150 mg, or up to about 140 mg, or up to about 130 mg, or up to about 120 mg, or up to about 110 mg, or up to about 100 mg, or may be in any range or amount therebetween. A total daily amount of the *Rhodiola rosea* extract (or active ingredients thereof) is often less than or about 300 mg, or may be less than or about 250 mg, or may be less than or about 240 mg, or may be less than or about 230 mg, or may be less than or about 220 mg, or may be less than or about 210 mg, or may be less than or about 200 mg. In one or more embodiments, the amount of *Rhodiola rosea* (or its active ingredients) in a single dose of a composition described herein is less than an amount found to be used in studies with extract from *Rhodiola rosea* alone for persons with stress and/or considered anxious and/or mild or moderately depressed, in which said doses were typically about 340 mg per day or up to 680 mg per day (given in at least two capsules, each containing about 170 mg). In one or more embodiments, the amount of *Rhodiola rosea* (or its active ingredients) provided with a daily dose of a composition described herein is less than an effective amount used in studies with *Rhodiola rosea* extract (or its active ingredients) when used alone for a person, such as a person having stress, anxiety, and/or mild or moderate depression, any of which may be associated with a difficulty controlling, regulating or losing weight.

The extract from *Astragalus membranaceus* or the third botanical substance is also known as *Astragalus propinquus* (*Astragalus* genus, Fabaceae family). The *Astragalus membranaceus* may be represented by an extract from the root of *Astragalus membranaceus*, including variety *mongholicus*. The extract from *Astragalus membranaceus* may comprise triterpenoid saponins (e.g., *acetylastragalosides, astragalosides, astragenol*), amino acids (e.g., GABA, l-canavaine), flavenoids, isoflavenoids, polysaccharides, plant sterols, volatile oil and selenium. The activities and/or effects related to administration of the *Astragalus membranaceus* extract and/or the active components thereof were described above. The astragalosides or cycloartane glycosides of the extract may be represented by formula I, and may include at least or more the cycloartane-type compounds, derivatives and analogues thereof, such as any one or more of the cycloartane compounds provided as formula II and formula III, depicted below, which may and have also been referred to as an astragaloside compound.

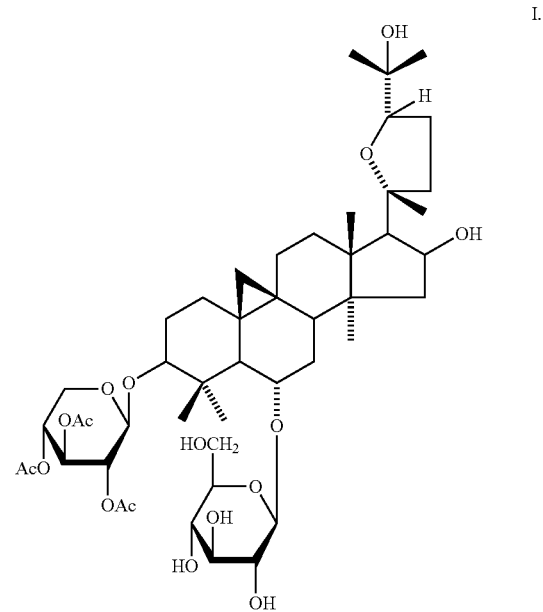

I.

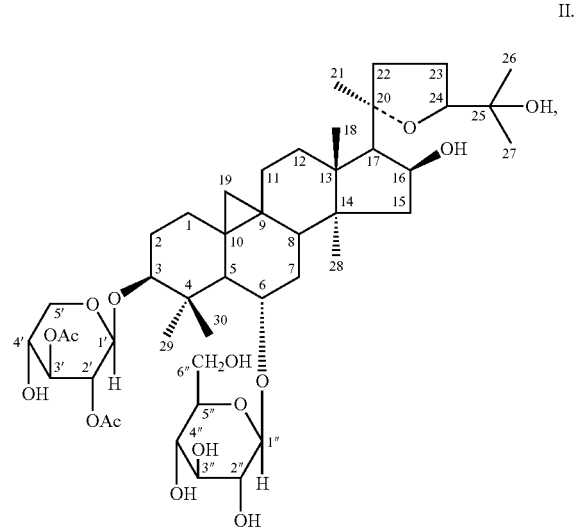

II.

III.

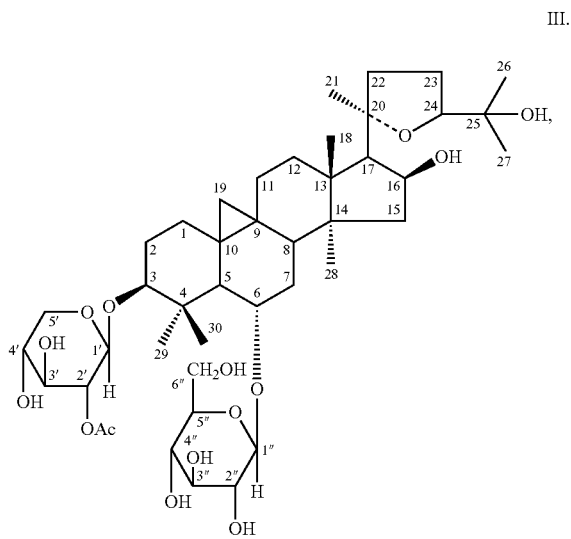

The astragaloside compound or cycolartane compound may also be of the formula depicted as Formula IV, shown below,

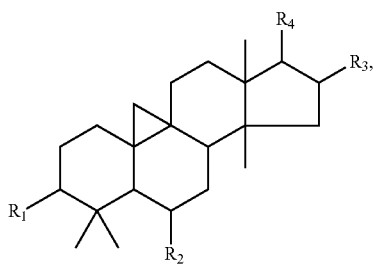

in which, for example, $R_1$ is selected from H, OH, O-acetyl, O-xylopyranosyl, O-(2-acetylxylopyranosyl), O-(3-acetylxylopyranosyl), O-(2,3-diacetylxylopyranosyl), O-(2,4-diacetylxylopyranosyl), O-xylopyranosyl-(1-2)-β-D-glucopyranosyl and O-xylopyranosyl-(1-2)-α-arabinopyranosyl; $R_2$ is selected from H, OH, O-acetyl and O-glucopyranosyl, O-xylopyranosyl; $R_3$ is selected from H, OH and O-acetyl; and $R_4$ is selected from structures including A, B, C, D, E, F.

A

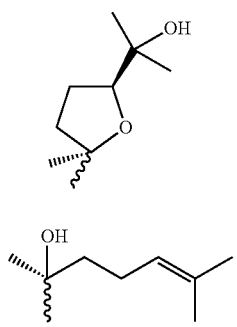

B

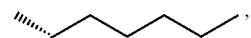

C

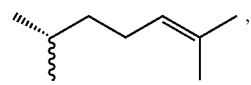

D

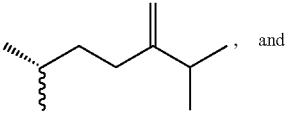

E

, and

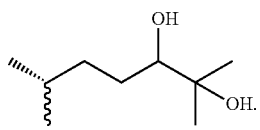

F

Preparation of useful astragaloside cycloartane compounds obtained from *Astragalus membranaceus* variety *mongholicus* are described at least in U.S. Pat. No. 8,197,860, which is incorporated herein by reference in its entirety, which also provides additional exemplary analogs and derivatives of the compound, and provides some of the astragaloside compounds and methods of obtaining them.

An astragaloside compound used alone or in combination with others and/or provided with or as the root extract of *Astragalus membranaceus* (such as variety *mongholicus*) and/or the root extract of *Astragalus membranaceus* may be used as the third botanical substance.

The extract from *Astragalus membranaceus* or the third botanical substance (and/or its active component(s), such as one or more astragaloside cycloartane compounds) should at least enhance transport of one or more amino acids (e.g., by enhanced absorption of the one or more amino acid in certain cells after delivery or administration of the third botanical substance). Facilitative transport of other nutrients may also be enhanced by the third botanical substance. Further properties have been described above. Said third botanical substance may be in an amount in a single dose of a composition described that is from about 1 mg to about 50 mg, or up to about 45 mg, or up to about 40 mg, or up to about 35 mg, or up to about 30 mg, or up to about 25 mg, or in any amount therebetween. In some embodiments, the amount of extract from *Astragalus membranaceus* (or its active component(s)) may be from about 10 mg to about 30 mg, or may be in any range or amount therebetween. A total daily amount of the extract from *Astragalus membranaceus* (or its one or more active component(s)) is often about or less than about 100 mg, or may be about or less than about 90 mg, or may be about or less than about 80 mg, or may be about or less than about 70 mg, or may be about or less than about 60 mg, or may be about or less than about 50 mg. In one or more embodiments, the amount of the extract from *Astragalus membranaceus* or its active component(s), such as one or more astragaloside cycloartane compounds, in a single dose of a composition described herein may be less or much less than an amount used effectively on its own for a person using the whole root extract alone, in which a dose for the person using the root extract alone was found to be effective at about 250 mg or up to 750 mg per day (given in one to three capsules, each containing about 250 mg).

The extract from *Panax notoginseng* or the fourth botanical substance is also known as *notoginseng*, three-seven root, mountain paint and San Qi (*Panax* genus, Araliaceae family). The *Panax notoginseng* may be represented by an extract from the root of *Panax notoginseng*. The extract from the root of *Panax notoginseng* may comprise flavenoids, glycans (panaxans), maltol, peptides, saponins (triterpene), vitamins (A, B6, other B vitamins), volatile oilzinc. The activities and/or effects related to administration of the *Panax notoginseng* extract and/or the active components thereof were described above. The triterpene saponins of the extract may be represented by formula V, a dammarane compound, and many include at least or more dammarane compounds, derivatives and analogues thereof, such as any one or more of the dammarane compounds provided as formula VI and formula VII, depicted below, which may and have been referred to as a ginsenoside compound.

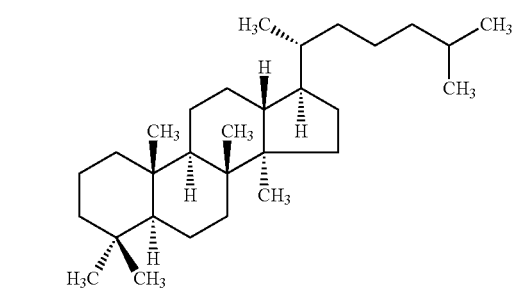

V.

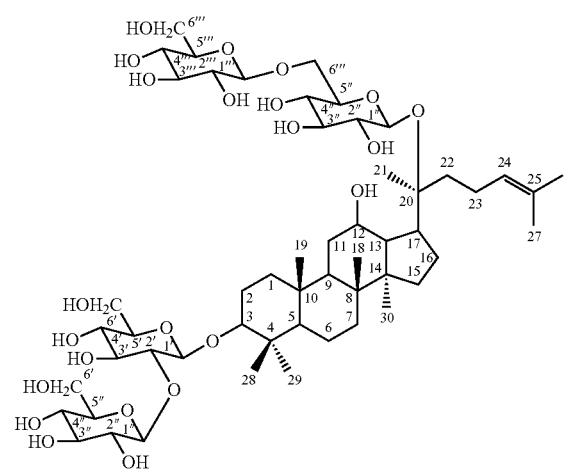

VI.

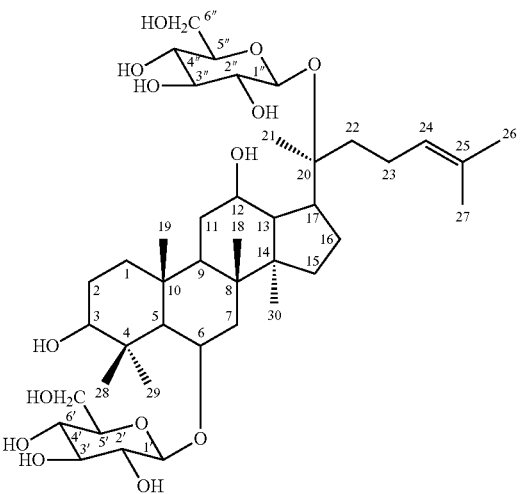

VII.

The ginsenoside may also be a dammarane compound of Formula VIII, shown below,

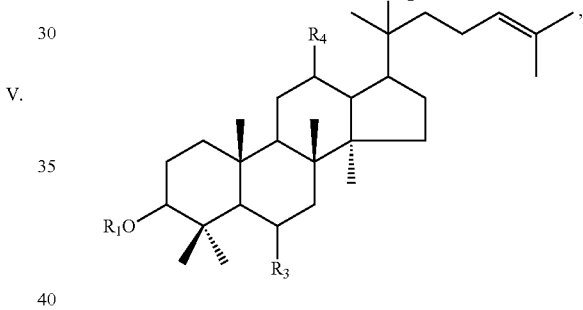

VIII in which, for example, $R_1$ is selected from H, acetyl, glucopyranosyl, glucopyranosyl-(2-1)-β-D-glucopyranosyl, glucopyranosyl-(2-1)-β-D-xylopyranosyl and glucopyranosyl-(2-1)-β-D-glucopyranosyl-(6-1)-xylopyranosyl; $R_2$ is selected from H, acetyl, glucopyranosyl, glucopyranosyl-(6-1)-β-D-glucopyranosyl, glucopyranosyl-(6-1)-β-D-xylopyranosyl, glucopyranosyl-(6-1)-α-L-arabinopyranosyl and glucopyranosyl-(6-1)-α-L-arabinofuranosyl; $R_3$ is selected from H, hydroxy, 0-acetyl, O-β-D-glucopyranosyl, O-β-D-glucopyranosyl-(2-1)-β-D-glucopyranosyl, O-β-D-glucopyranosyl-(2-1)-β-D-xylopyranosyl and O-β-D-glucopyranosyl-(2-1)-α-L-rhamnopyranosyl; and $R_4$ is selected from H, hydroxyl and O-acetyl.

Preparation of useful ginsenoside dammarane compounds obtained from *Panax notoginseng* are described at least in U.S. Publication No. 20060293255, which is incorporated herein by reference in its entirety, which also provides additional exemplary analogs and derivatives of the compound, and provides some useful ginsenoside dammarane and methods of obtaining them.

A ginsenoside and/or dammarane compound used alone or in combination with others and/or provided with or as the root extract of *Panax notoginseng* and/or the root extract of *Panax notoginseng* may be used as the fourth botanical substance.

The extract from *Panax notoginseng* or the fourth botanical substance (and/or its active component(s), such as one or more ginsenoside or dammarane compounds described above) should at least facilitate transport of one or more amino acids (e.g., by enhanced absorption of the one or more amino acid in certain cells after delivery or administration of the fourth botanical substance). Facilitative transport of other nutrients may also be enhanced by the fourth botanical substance. Furthers activities of the fourth botanical substance have been described above. Said fourth botanical substance may be in an amount in a single dose of a composition described that is from about 1 mg to about 50 mg, or up to about 45 mg, or up to about 40 mg, or up to about 35 mg, or up to about 30 mg, or up to about 25 mg, or in any amount therebetween. In some embodiments, the amount of extract from *Panax notoginseng* (or its active component(s) including the one or more ginsenosides) may be from about 10 mg to about 30 mg, or may be in any range or amount therebetween. A total daily amount of the extract from *Panax notoginseng* (or its one or more active component(s)) is often about or less than about 100 mg, or may be about or less than about 90 mg, or may be about or less than about 80 mg, or may be about or less than about 70 mg, or may be about or less than about 60 mg, or may be about or less than about 50 mg. In one or more embodiments, the amount of the extract from *Panax notoginseng* or its active component(s) as described, such as one or more ginsenoside and/or dammarane compounds, in a single dose of a composition described herein may be less than or much less than an amount found to be effective for a person using the whole root ground powder alone, in which a dose for the person was found to be effective at upwards of 1 to 3 g or 5 to 10 g per day (as a powder or mixed in water).

The third and fourth botanical substances may be provided as a blend of said third and fourth botanical substances, in which the blend comprises up to about 50% of the third botanical substance (e.g., the extract from *Astragalus membranaceus* or its active component(s), such as one or more astragaloside cycloartane compounds) and up to about 50% of the fourth botanical substance (e.g., the extract from *Panax notoginseng* or its active component(s), such as one or more ginsenoside dammarane compounds). In such a blend, the third botanical substance may be in an amount that is between about 10% and 50%, or may be in an amount that is between about 40% to 50%. The fourth botanical substance may be in an amount in the blend that is between about 10% and 50%, or may be in an amount in the blend that is between about 40% to 50%. In such a blend, an excipient (e.g., such as one or more of an absorbent, disintegrant and/or sweetener) may also be present as the remaining ingredient, generally in an amount that is less than 10%, or is between about 1% and 10%, or may be at or about 5% of the blend. A suitable example of an excipient is maltodextrin (preferably GMO free). One example of a blend providing the third and fourth botanical substances is AstraGin® (registered with Nuliv Science USA, Inc., California, USA), which contains a blend of between about 45% to 50%, of the third botanical substance (as an astragaloside compound extracted from *Astragalus membranaceus* variety *mongholicus*) and about the same amount of the fourth botanical substance (as a ginsenoside compound extracted from *Panax notoginseng*). In some embodiments the amount of the third botanical substance and the amount of the fourth botanical substance may be about the same. In some embodiments, the amounts of the third and fourth botanical substances when provided in the blend differ from the amounts described above. For example, when the third and fourth botanical substances are provided in a blend, the amount of the blend for one or a single administration may be up to about 75 mg, or may be between about 25 mg and 50 mg, or in any range therebetween. In said blends with the amounts provided for the single administration, the third and fourth botanical substances may each be at least about 40% of the blend and each may be up to about 50% of the blend, the blend then being added to include both the third and fourth botanical substance in a composition described herein.

The extract from black pepper or the fifth botanical substance may include an extract from the peppercorns of a pepper plant (*Piper* genus, Piperaceae family). The extract may also be represented as piperine, its isomers and/or analogs, and/or capsaicin, its isomers and/or analogs. The activities of the black pepper extract have been described above. The extract of black pepper and/or active ingredients from the extract are generally in an amount in a single dose of a composition described herein that is from about 1 mg to about 30 mg, or up to about 25 mg, or up to about 20 mg, or up to about 15 mg, or up to about 10 mg, or may be in any range or amount therebetween. A total daily amount of the black pepper extract (or active ingredients thereof) is often less than or about 60 mg, or may be less than or about 50 mg, or may be less than or about 40 mg, or may be less than or about 30 mg, or may be less than or about 20 mg. In one or more embodiments, the amount of the black pepper extract (or active ingredients thereof) in a single dose of a composition described herein may be about or less than an amount found to be used effectively in persons given the black pepper extract alone as a supplement.

The novel compositions described herein will often further include a combination of amino acids and/or amino acid precursors. The combination of the amino acids and/or amino acid precursors may include but are not limited to tyrosine or acetyl L-tyrosine, phenylalanine, theanine, hydroxytryptophan (5-HTP), and phenylethylamine.

Tyrosine may be provided as acetyl-L-tyrosine, L-tyrosine, or other alternatives or analogs. The amino acid is also referred to as L-2-Amino-3-(4-hydroxyphenyl)propanoic acid. It may be provided in its naturally occurring form or as a chemical precursor. The activities and/or effects related to administration of the tyrosine or acetyl-L-tyrosine and/or suitable analogs thereof were described above. Tyrosine or acetyl-L-tyrosine (or a suitable analog thereof) is generally included in the composition in an amount in a single dose of the composition described herein that is from about 100 mg to about 400 mg, or up to about 350 mg, or up to about 300 mg, or up to about 250 mg, or may be in any range or amount therebetween. A total daily amount of the tyrosine or acetyl-L-tyrosine (or suitable forms or analogs thereof) is often less than or about 800 mg, or may be about or less than about 750 mg, or may be about or less than about 700 mg, or may be about or less than about 650 mg, or may be about or less than about 500 mg.

Phenylalanine may be provided in its naturally occurring form, as a chemical precursor, or as DL phenylalanine (a mixture of D and L phenylalanine), or other alternatives or analogs. The amino acid is also referred to as 2-Amino-3-phenylpropanoic acid. The activities and/or effects related to administration of the phenylalanine or DL phenylalanine and/or suitable analogs thereof were described above. Phenylalanine or DL phenylalanine or any suitable analog is generally included in the composition in an amount in a single dose of the composition described herein that is from about 50 mg to about 300 mg, or up to about 250 mg, or up to about 200 mg, or up to about 150 mg, or may be in any range or amount therebetween. A total daily amount of the phenylalanine or DL phenylalanine (or suitable forms or analogs thereof) is often less than or about 600 mg, or may be about or less than about 650 mg, or may be about or less than about 500 mg, or may be about or less than about 450 mg, or may be about or less than about 400 mg, or may be about or less than about 350 mg, or may be about or less than about 300 mg.

Theanine may be provided as N-ethyl-L-glutamine or as an analog of L-glutamate and L-glutamine, or other suitable alternatives or analogs. It may be provided in its naturally occurring form or as a chemical precursor. It may be provided or extracted from tea leaves, Camellia sinensis, and/or from mushrooms, Boletus badius. The amino acid is also referred to as N-ethyl-L-glutamine; (2S)-2-ammonio-5-(ethylamino)-5-oxopentanoate. The effects of theanine are described above. Theanine (or its analog) is generally included in the composition in an amount in a single dose of the composition described herein that is from about 25 mg to about 250 mg, or up to about 200 mg, or up to about 150 mg, or up to about 100 mg, or may be in any range or amount therebetween. A total daily amount of the theanine (or suitable forms or analogs thereof) is often less than or about 500 mg, or may be about or less than about 450 mg, or may be about or less than about 400 mg, or may be about or less than about 350 mg, or may be about or less than about 300 mg, or may be about or less than about 250 mg, or may be about or less than about 200 mg. The amount of theanine may be provided in a dose that is less or significantly less than a dose found effective in a person who is provided the theanine alone, said dose being as much as 1200 mg per day.

Hydroxytryptophan (5-HTP) or oxitriptan may be provided in its naturally occurring form or as a chemical precursor. The amino acid is also referred to as 2-amino-3-(5-hydroxy-1H-indol-3-yl)propanoic acid. The effects of hydroxytryptophan are described above. Hydroxytryptophan (or its analog) is generally included in the composition in an amount in a single dose of the composition described herein that is from about 10 mg to about 100 mg, or up to about 90 mg, or up to about 80 mg, or up to about 70 mg, or up to about 60 mg, or up to about 50 mg, or may be in any range or amount therebetween. A total daily amount of the hydroxytryptophan (or suitable forms or analogs thereof) is often less than or about 200 mg, or may be about or less than about 150 mg, or may be about or less than about 100 mg.

Phenylethylamine may be provided in its naturally occurring form or as a chemical precursor or suitable analog thereof. The amino acid is also referred to as β-phenylethylamine or 2-phenylethylamine. The effects of phenylethylamine (or suitable forms or analogs thereof) are described above. Phenylethylamine (or its analog) is generally included in the composition in an amount in a single dose of the composition described herein that is from about 50 mg to about 350 mg, or up to about 300 mg, or up to about 250 mg, or up to about 200 mg, or up to about 175 mg, or may be in any range or amount therebetween. A total daily amount of the phenylethylamine (or suitable forms or analogs thereof) is often less than or about 400 mg, or may be about or less than about 350 mg, or may be about or less than about 300 mg, or may be about or less than about 250 mg, or may be about or less than about 200 mg.

The novel compositions described herein further include one or more metals. The metals include but are not limited to transition metals (e.g., chromium) and alkaline earth metals (e.g., calcium). Said metals are provided in suitable valences to prevent toxicity. For example, chromium is provided as trivalent chromium (e.g., chromium (III) nicotinate). The activities and/or effects of chromium (or suitable forms thereof) are described above. Chromium may be included in the composition in an amount in a single dose of the composition described herein that is from about 50 micrograms to about 200 micrograms, or up to about 200 micrograms, or up to about 180 micrograms, or up to about 160 micrograms, or up to about 140 micrograms, or up to about 120 micrograms or may be in any range or amount therebetween. A total daily amount of the chromium (or suitable forms or analogs thereof) is often less than or about 400 micrograms, or may be about or less than about 350 micrograms, or may be about or less than about 300 micrograms, or may be about or less than about 250 micrograms, or may be about or less than about 200 micrograms. Calcium may be included in the composition in an amount in a single dose of the composition described herein that is from about 20 mg to about 100 mg, or up to about 100 mg, or up to about 80 mg, or up to about 60 mg, or up to about 50 mg, or may be in any range or amount therebetween. A total daily amount of the calcium (or suitable forms or analogs thereof) is often less than or about 100 mg, or may be about or less than about 80 mg, or may be about or less than about 70 mg, or may be about or less than about 60 mg, or may be about or less than about 50 mg.

The novel compositions described herein may and often further include one or more vitamins. Suitable vitamins include Vitamins B-6 and B-12. Additional vitamins and/or omega-3 or omega-6 fatty acids may also be included in the compositions described herein. The effects and/or activities of vitamins, such as the B vitamins are described above. For example, Vitamin B-12 may be included in the composition in an amount in a single dose of the composition described herein that is from about 1 micrograms to about 15 micrograms, or up to about 15 micrograms, or up to about 12 micrograms, or up to about 10 micrograms, or up to about 8 micrograms, or up to about 6 micrograms or may be in any range or amount therebetween. A total daily amount of the Vitamin B-12 (or suitable forms or analogs thereof) is often less than or about 15 micrograms, or may be about or less than about 12 micrograms, or may be about or less than about 10 micrograms, or may be about or less than about 8 micrograms, or may be about or less than about 6 micrograms. Vitamin B-6 (pyridoxal phosphate or variations an analogs thereof) may be included in the composition in an amount in a single dose of the composition described herein that is from about 2 mg to about 20 mg, or up to about 20 mg, or up to about 18 mg, or up to about 16 mg, or up to about 14 mg, or up to about 12 mg, or up to about 10 mg, or may be in any range or amount therebetween. A total daily amount of the Vitamin B-6 (or suitable forms or analogs thereof) is often less than or about 20 mg, or may be about or less than about 18 mg, or may be about or less than about 16 mg, or may be about or less than about 14 mg, or may be about or less than about 12 mg, or may be about or less than about 10 mg. In some embodiments, up to 100% of a daily recommended amount of one or more vitamins may be included in the compositions described herein.

The novel compositions described herein may and often further include caffeine. However, caffeine may be excluded from certain compositions when additional energy associated with caffeine is not desirable. The caffeine described herein when provided is generally provided as a xanthine alkaloid or a methylated form (methyl xanthine alkaloid) or derivatives thereof, such as guaranine, mateine, and/or theine. Further non-limiting examples include but are not limited to theobromine, theophylline and a synthetic analog aminophylline (theophylline ethylenediamine) (with or without methylation). Esters and salts thereof may comprise a malate. The caffeine is not limited to an anhydrous powder form, any salt or derivative of caffeine, as described above, or an equivalent, including a compounded equivalent that is non-toxic and pharmaceutically acceptable may be used. The caffeine or its equivalent should bind to adenosine receptors, antagonize certain adenosine receptors, and/or increase levels of cyclic AMP. Additional activities and/or effects of caffeine are described above. In addition or as an alternative, plant sources of caffeine may be provided, such as from guarana, kola nut, Yerba mate, green or black tea, and/or cacao pods. In total, the amount of caffeine in a final composition will generally not exceed 70 mg in a single administration. The caffeine content in the composition described herein, such as a composition for a single dose of the composition, may be between about 10 mg and 100 mg, or in any range or amount therebetween. A total daily amount of the caffeine (or suitable forms or analogs thereof) is often less than or about 120 mg, or often less than or about 100 mg, or may be about or less than about 90 mg, or may be about or less than about 80 mg, or may be about or less than about 70 mg, or may be about or less than about 60 mg, or may be about or less than about 50 mg.

In addition, a stilbenoid compound may be included in the compositions described herein. The stilbenoid compound may also be a synthetic form of the natural compound or extracted from a natural source (e.g., tree bark, small berries, etc.), or a suitable and effective analog or derivative thereof, that is a phytoalexin, acting as an antioxidant, which may provide other actions (e.g., anti-cancer activity, lowering triglyceride levels, as examples). The stilbenoid compound may also provide positive effects on mental clarity and/or memory. Suitable examples of the stilbenoid compound are depicted as formula IX and formula X, in which formula IX is resveratrol and formula IX is pterostilbene.

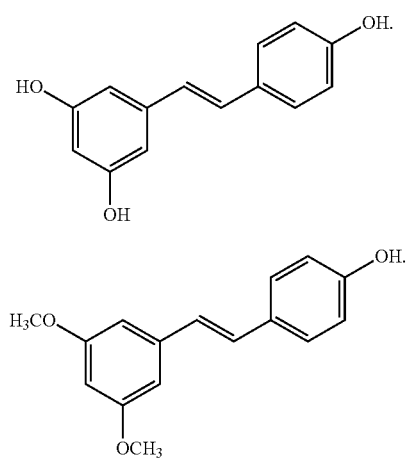

In one or more forms the stilbenoid composition may be provided in a co-crystalline form with caffeine, including but not limited to co-crystals as described in U.S. Pat. Nos. 8,318,807, 8,399,712, 8,415,507, 8,513,236, each of which is incorporated herein by reference in its entirety, or as is described in WO 20100141107, which is herein incorporated by reference in its entirety. The crystalline form of the stilbenoid compounds should improve bioavailability and/or absorption well as dissolution and solubility, as compared with the amorphous forms, and may when co-crystallized with caffeine improve absorption of caffeine, such that the amount of caffeine may be further reduced to an amount at or less than 70 mg in a single administration, that is at or less than 50 mg in a single administration, or that is at or less than 40 mg in a single administration, or that is at or less than 30 mg in a single administration, or that is at or less than 20 mg in a single administration. The stilbenoid compound provided alone or in a co-crystalline form with caffeine will often be provided in a similar amount as the caffeine. When in a co-crystalline form, the molar ratio of the stilbenoid compound and caffeine may be at or about 1:1, or may include more stilbenoid compound than caffeine or may consist of more caffeine than stilbenoid compound. One representative example of co-crystalline form suitable to provide in compositions described herein is Purenergy™ (ChromoDex Inc., California, USA), which contains about 41-46% caffeine, and 54-60% pterostilbene.

The novel compositions described herein may further include nicotinamide riboside, which may also be provided as a thereof, or as a precursor of nicotinamide adenine dinucleotide (NAD). The nicotinamide riboside (and/or one or more NAD precursors) may be included to reduce low density lipoproteins and free fatty acids (reduce cholesterol levels) and may further increase metabolism of fat. It is possible that deficiency of NAD may be an unexpected consequence of having low metabolism. Thus, including nicotinamide riboside (and/or one or more NAD precursors) should improve overall metabolism. The amount of the nicotinamide riboside (or suitable forms or analogs thereof, or a precursor thereof or as a precursor of NAD) in the compositions described herein, such as in any composition described herein for a single dose of the composition, may be between about 75 mg and 200 mg, or in any range or amount therebetween. For example, the range of the nicotinamide riboside (or a precursor thereof or as a precursor of NAD) in a composition described herein may be an amount that is about 75 mg to 100 mg. A total daily amount of the nicotinamide riboside (or suitable forms or analogs thereof, or a precursor thereof or as a precursor of NAD) is often less than or about 400 mg, or may be about or less than about 350 mg, or may be about or less than about 300 mg, or may be about or less than about 250 mg, or may be about or less than about 200 mg, or may be about or less than about 150 mg. One representative example of nicotinamide riboside suitable to provide in compositions described herein is Niagen® (registered with ChromoDex Inc., California, USA). The dose in a single administration as described herein may be less than an amount offered by suppliers to provide an effect, in which doses of 250 mg per day, and often at least 500 mg or 750 mg per day of nicotinamide riboside are reported by others to be effective.

The novel compositions described herein may further include one or more components that stimulate ATP production. One example has trace minerals extracted from plants (e.g., peat) combined with a fruit extract. A representative example of such a component suitable for use in compositions described herein is available as ElevATP® (registered with VDF FutureCeuticals, Inc., Illinois, USA), in which an amount included is one that elicits said effects.

In some embodiments, the botanical substances described above may comprise up to about 20 wt. % of a final composition, when prepared, for one or a single administration. In some embodiments, the botanical substances in a final composition will comprise between about 8% by weight and about 20% by weight of the final composition when prepared for one or a single administration. Alternative amounts are also suitable and contemplated in the compositions described herein. For example, in some embodiments, the botanical substances described above may comprise up to about 10 wt. % of a final composition, when prepared, for one or a single administration. In some embodiments, the botanical substances in a final composition will comprise between about 2 wt. % and about 10 wt. % of the final composition when prepared for one or a single administration.

In some embodiments, the amino acids described above may comprise up to about 60 wt. % of a final composition, when prepared, for one or a single administration. In some embodiments, the amino acids in a final composition will comprise between about 40% by weight and about 60% by weight of the final composition when prepared for one or a single administration. Of course alternative amounts are also suitable for use in the compositions described herein. For example, in some embodiments, the amino acids described above may comprise up to about 20 wt. % of a final composition, when prepared, for one or a single administration. In some embodiments, the amino acids in a final composition will comprise between about 5 wt. % and about 20 wt. % of the final composition when prepared for one or a single administration.

In some embodiments, the metals described above may comprise up to about 10 wt. % of a final composition, when prepared, for one or a single administration. In some embodiments, the metals in a final composition will comprise between about 1% by weight and about 10% by weight of the final composition when prepared for one or a single administration. Alternative amounts are also suitable and contemplated in the compositions described herein. For example, in some embodiments, the metals described above may comprise up to about 5 wt. % of a final composition, when prepared, for one or a single administration. In some embodiments, the metals in a final composition will comprise less than 1 wt. % of the final composition when prepared for one or a single administration.

In some embodiments, the vitamins described above may comprise up to about 4 wt. % of a final composition, when prepared, for one or a single administration. In some embodiments, the vitamins in a final composition will comprise between about 0.1% by weight and 4% by weight of the final composition when prepared for one or a single administration. Alternative amounts are also suitable and contemplated in the compositions described herein. For example, in some embodiments, the vitamins described above may comprise less than 1 wt. % of a final composition, when prepared, for one or a single administration. In some embodiments, the vitamins in a final composition will comprise less than 0.5 wt. % of the final composition when prepared for one or a single administration.

In some embodiments, the caffeine described above may comprise up to about 5 wt. % of a final composition, when prepared, for one or a single administration. In some embodiments, the caffeine in a final composition will comprise between about 1% by weight and 5% by weight of the final composition when prepared for one or a single administration. Alternative amounts are also suitable and contemplated in the compositions described herein. For example, in some embodiments, the caffeine described above may comprise up to about 2 wt. % of a final composition, when prepared, for one or a single administration. In some embodiments, the caffeine in a final composition will comprise between about 0.5 wt. % and about 2 wt. % of the final composition when prepared for one or a single administration.

The balance of many of the compositions described herein may include one or more excipients. In some embodiments, the excipients may comprise between about 25 wt. % to about 40 wt. % of a final composition, when prepared, for one or a single administration. In some embodiments, the excipients in a final composition will comprise between about 70 wt. % to about 85 wt. % of the final composition when prepared for one or a single administration. Of course alternative amounts are also suitable for use in the compositions described herein depending on the final weight and form of the composition, as understood by those of skill in preparing formulations.

The compositions described herein include at least a combination of some or all of the components described above. For example, compositions described herein may include some or all of the described botanical substances (e.g., extracts), some or all of the described amino acids (and/or as amino acid precursors), and some or all of the described metals. In some embodiments, compositions described herein will include some or all of the described botanical substances (e.g., extracts), some or all of the described amino acids (and/or as amino acid precursors), some or all of the described metals, and caffeine. In some embodiments, compositions described herein will include some or all of the described botanical substances (e.g., extracts), some or all of the described amino acids (and/or as amino acid precursors), some or all of the described metals, and some or all of the described vitamins. In some embodiments, compositions described herein will include some or all of the described botanical substances (e.g., extracts), some or all of the described amino acids (and/or as amino acid precursors), some or all of the described metals, some or all of the described vitamins, and caffeine. Further components may be provided in compositions described herein, such as nicotinamide riboside, or a precursor nicotinamide adenine dinucleotide (NAD). Having said combination of components provides a multi-targeted approach to control and/or regulation of appetite, in which the person or subject provided any of the compositions described herein is effectively supplemented with a plurality of biologically active components, in which, independently, each component on its own generally provides some bioactivity or biologic effect. In combination, said components behave synergistically or at least provide one or more biologic effects that are better than would be predicted from the biologic activity of the independent component when used alone. Unexpectedly, the synergistic effect is provided. In many embodiments, the synergistic effect is greater than would be predicted.

For administration of any of the compositions described herein, each single administration may generally provide all of the combination of components in a single administration. However, co-administration of certain components is also contemplated. The co-administration may occur by providing all of the components in a single formulation, or independently, or in a variety of blends. Some or all of the components may be provided sequentially or concomitantly. The compositions described herein may also comprise various co-formulations having two or more of the described components. Said co-formulations may be taken simultaneously or concomitantly, or sequentially.

In one or more preferred embodiments, one or a single administration as described herein may be provided as a tablet or capsule or powder or in a liquid. The one or a single dose may be provided before or after a meal. It is often taken without food. In some embodiments, one dose (or single administration) is provided per day. For example, the one dose (or single administration) may be provided one time per day, before or after a lunch time meal or before or after an early dinner time meal. In some embodiments, two doses (two independent administrations) are provided per day. For example, a first dose (or first administration) may be provided one time before or after an afternoon meal (e.g., lunch time) and a second dose (or second administration) may be provided one time before or after an evening meal (e.g., early dinner, or dinner time). In some embodiments, the one or a single administration comprises one tablet. In some embodiments, the one or a single administration comprises two or more tablets. In some embodiments, the one or a single administration comprises a powder to be taken as is or mixed in a liquid, such as water. In some embodiments, it is preferred that the compositions described herein are administered without food. In some embodiments, it is preferred that the compositions described herein are administered before a meal. In some embodiments, it is preferred that the compositions described herein are administered up to about 30 minutes before a meal, or up to about 45 minutes before a meal, or in some range therebetween, or no more than 1 hour before a meal. Compositions described herein may also be are administered up to about 30 minutes after a meal, or up to about 45 minutes after a meal, or in some range therebetween, or no more than 1 hour after a meal.

The excipients when included assist in providing the compositions in any of its various forms (e.g., solid form, or semi-solid forms, powder or liquid). The excipients may facilitate transmembrane transport of the compositions, or portions thereof.

The excipients when included may generally comprise one or more of a sugar alcohol, organic acid, alkalizing agent or pH buffering agent, absorbent or disintegrant or glidant, soluble fiber, flavorant and/or sweetener. Representative and non-limiting examples of the sugar alcohol includes mannitol, xylitol, sorbitol, erythritol, pyranose derivatives, and furanose derivatives thereof. Representative and non-limiting examples of the organic acids include tartaric acid, malic acid acetic acid, benzoic acid, ascorbic acid, citric acid, sorbic acid, and hydrochloric acid, as well as salts thereof (often as sodium or potassium salts). Representative and non-limiting examples of the alkalinizing agent and/or pH buffering agent include sodium citrate, potassium citrate, sodium benzoate, potassium sorbate. Representative and non-limiting examples of the absorbent or disintegrant and/or glidant includes silica, such as a colloidal silica or amorphous colloidal silicon dioxide. Sweeteners may include, for example but not limited to, sugar, sucralose, acesulfame potassium, *stevia*. Sweeteners may be absent when the compositions described herein are provided as a solid or in solid form. Sugar as a sweetener will be absent for many or preferred compositions described herein. Colorants may be from natural sources, and/or provided by one or more natural flavorings. The one or more excipients may serve as pharmaceutical carriers. Accordingly, compositions described herein for administration to a person generally include one or more excipients or pharmaceutical carriers, some or many of which may serve as bulking agents, fillers, flavorants, and/or natural preservatives. In some embodiments, the compositions described include only natural components or ingredients, or only components or ingredients that are analogous to or derived from ingredients or components obtained from nature.

In one or more embodiments, the compositions described herein, including any excipients or pharmaceutical carriers, are considered Generally Recognized as Safe (GRAS) in accordance with the Federal Food, Drug and Cosmetic Act. The compositions described herein, including any excipients or pharmaceutical carriers, will generally not include products prepared by or produced by genetically modified organisms (GMO). In some embodiments, all components provided in the novel compositions described herein, and hence the novel compositions themselves, will be GMO free. In some embodiments, such as powder forms and liquids, the compositions will generally be free of or substantially free of cellulose, pectin, talc, or gelatin. In most embodiments, the composition will generally be free of or substantially free of polyesters and polyimides, methacrylate polymers or copolymers as well as cross-linked polymers. In most embodiments, the compositions will generally be free of or substantially free of surfactants and detergents. In most embodiments, the compositions will generally be free of or substantially free of chelators. In most embodiments, the composition will generally be free of or substantially free of prescription drugs, such as those synthesized without being a direct analog, derivative or prodrug of a naturally existing compound or molecule as described herein. In one or more embodiments, the compositions will generally be free of or substantially free of glycols. In one or more embodiments, the compositions will generally be free of or substantially free of glycerols. In some embodiments, the compositions will generally be free of or substantially free of stearates. In some embodiments, the final formulation for a single administration will be considered to have fewer than 10 or fewer than 20 carbohydrates from sugar. Some compositions may contain a fiber additive. Some compositions will contain no dietary fiber. In some embodiments, the final formulation, even when prepared for a single administration, will be considered to have about or less than about 20 calories, or about or less than about 10 calories, with no calories from fat in the single administration.

Compositions as described herein may be provided in a solid, dry form; such a solid may include but is not limited to a tablet, capsule, caplet, beads, granules, particles, powder, crystals, film, losenge, or wafer. Compositions as described herein may be provided in a semi-solid form; such forms include but not limited to a resinate, a waxate, a gum, a film, a losenge or a wafer or provided inside a capsule or caplet. Compositions as described herein may be provided in a liquid form, in which the composition is in a concentrated form to be diluted by a liquid and in a ready-to-drink form.

Unexpectedly, the described compositions have been found to have a robust and unexpected synergistic effect, greater than the activity of each of the individual components or at least some of the individual components when said individual components are used alone. In one or more embodiments, the amount of at least some of the individual components is less or much less than when used alone or clinically by others to provide their effect. The magnitude of synergism as found with the described compositions (having any of the novel combinations described herein) was not predicted.

A first representative formulation for a composition described herein is shown in TABLE 1, representing a composition provided in the form of a tablet. The tablet is provided as a single dose for oral administration. The single dose includes 1 tablet having about 1450 mg/tablet.

TABLE 1

| | One administration (1450 mg) | |
|---|---|---|
| | Amount (mg) | % |
| Botanical substances | | |
| Crocus extract | 30 | 2.1 |
| Rhodiola rosea extract | 100 | 6.9 |
| extracts of Astragalus membranaceus and Panax notoginseng | 50 | 3.4 |
| Black pepper extract | 3 | 0.2 |
| Amino Acids | | |
| acetyl L-tyrosine | 250 | 17.2 |
| DL phenylalanine | 150 | 10.3 |
| theanine | 100 | 6.9 |
| hydroxytryptophan | 50 | 3.4 |
| phenylethylamine | 175 | 12.1 |
| Metals | | |
| Chromium polynicotinate | 120 mcg | ~0.008 |
| calcium | 50 | 3.4 |
| Vitamins | | |
| Vitamin B-6 | 10 | 0.7 |
| Vitamin B-12 | 6 mcg | <0.001 |
| Caffeine | 40 | 2.8 |
| Total | ~960 | ~66.2 |

Additional ingredients in the formulation depicted in TABLE 1 included at least dicalcium phosphate, cellulose (e.g., microcrystalline and/or hydroxypropyl methylcellulose), magnesium stearate, silica, croscarmellose sodium, and stearic acid.

A second representative formulation for a composition described herein is shown in TABLE 2, representing a composition provided as a powder. The powder is provided as a single dose for oral administration. The powder is for dissolving in a liquid or water for drinking. The single dose includes about 5 gm.

TABLE 2

| | One administration (5 g) | |
|---|---|---|
| | Amount (mg) | % |
| Botanical substances | | |
| Crocus extract | 30 | 0.6 |
| Rhodiola rosea extract | 100 | 2.0 |
| extracts of Astragalus membranaceus and Panax notoginseng | 50 | 1.0 |
| Black pepper extract | 10 | 0.2 |
| Amino Acids | | |
| acetyl L-tyrosine | 250 | 5.0 |
| DL phenylalanine | 150 | 3.0 |
| theanine | 100 | 2.0 |
| hydroxytryptophan | 50 | 1.0 |
| phenylethylamine | 175 | 3.5 |
| Metals | | |
| Chromium polynicotinate | 120 mcg | ~0.002 |
| Vitamins | | |
| Vitamin B-6 | 2 | 0.04 |
| Vitamin B-12 | 6 mcg | ~0.0001 |
| Caffeine | 40 | 0.8 |
| Total | ~1008 | ~20.14 |

Other ingredients in the formulation depicted in TABLE 2 included at least one sweetener (as a sugar substitute), soluble fiber, a buffering acid, natural flavors, natural color and silica.

In some embodiments, the compositions are admixed together. The compositions when combined to include the various botanical substances, amino acids, and metal(s) with or without the vitamins, caffeine, and excipients may form a co-blend. In some embodiments, amino acids are granulated independently and then combined with the other components. Generally, any order of admixing and/or co-blending of said components is acceptable, using processes known in the relevant art. In some embodiments, the composition may be compressed, such as to form a solid (e.g., tablet) after admixing or co-blending. In some embodiments, the composition may be coated with a coating. Suitable coating ingredients, include but are not limited to dicalcium phosphate, microcrystalline cellulose, stearic acid, hydroxypropyl methylcellulose, croscarmellose sodium, silica, polydextrose, titanium dioxide, talc, colorant (e.g., FD&C Blue 2), maltodextrin, and medium chain triglycerides.

Administration of any of the compositions described herein may when desired be optimized by pharmacodynamic and pharmacokinetic data, thereby achieving a better effect and/or outcome for a person.

When compositions as described herein in TABLE 1 were provided to representative subjects, such as subjects desiring weight control or weight loss or control and/or regulation of appetite, the compositions were generally provided daily to each subject daily, up to about or at about 30 minutes or up to about 45 minutes before an afternoon meal (e.g., lunch) and before an evening meal (e.g., dinner). The compositions were thus provided twice a day. The subjects continued the described administration for 90 days. The subjects all reported a significant loss in weight after use of the composition described herein for the 90 days. In these subjects, the composition comprising the described components were provided so that all the components of the composition were included in the same composition and said composition was provided to the subject orally. Appetite control and regulation, satiation, loss of cravings, reductions in anxiety and fatigue, as well as concomitant weight loss was observed by all the subjects who were administered one of the compositions described herein.

In a first subject, a 40 yr. old Caucasian male, given a composition described herein and in the manner described above for 90 days without any further modification in either diet or exercise routine, a loss in weight of 30 pounds in the 90 days was obtained by the first subject.

In a second subject, a 47 yr. old female (mixed race: African American and Caucasian) in early stages of menopause with significant symptomology and given a composition described herein in the manner described above for the 90 days, the second subject experienced a weight loss of 27 pounds in the 90 days. The subject did not undergo any modification in their existing diet or exercise routine. The weight loss was accompanied by a reduction in size (circumference) around the hips of 3 inches, a reduction in waist size (circumference) of 4.5 inches, and a reduction is bust size (circumference) of 2.5 inches, a reduction in thigh width (circumference) of 3 inches, and a reduction in circumferential width of the upper arm of 2.5 inches.

In a third subject, a 42 yr. old Caucasian female suffering from Ankylosing Spondylitis (an autoimmune disease) was given a composition described herein in the manner described above for the 90 days. The third subject experienced a weight loss of 30 pounds in the 90 days. The weight loss was accompanied by a reduction in the waist (circumference) of 5 inches, a reduction around the hips (circumference) of 4 inches, a reduction in bust size (circumference) of 3.5 inches and a reduction in thigh circumference of 3.2 inches. The third subject made no modifications to the existing diet or exercise routine because of her disease condition.

In a fourth subject, a 54 yr. old Caucasian female given a composition described herein in the manner described above for at least 90 days, the fourth subject experienced a weight loss of 22 pounds in the 90 days without making modifications to the existing diet or exercise routine. The weight loss was accompanied by a reduction in the waist (circumference) of 6 inches, a reduction around the hips (circumference) of 2 inches, a reduction in thigh circumference of 2 inches, and a reduction in upper arm circumference of 1.5 inches. A calculation of body fat showed a 7% loss in body fat.

In a fifth subject, a 55 yr. old Caucasian male given a composition described herein in the manner described above for the 90 days, the fifth subject experienced a weight loss of 31.6 pounds in the 90 days without making modifications to the existing diet or exercise routine. The weight loss was accompanied by a reduction in the waist (circumference) of 3.5 inches, a reduction around the chest (circumference) of 3 inches, a reduction around the hips (circumference) of 4.5 inches, a reduction in thigh circumference of 1.5 inches, and a reduction in upper arm circumference of 1 inches. A calculation of body fat showed a 5.7% loss in body fat.

All of the examples show that the unique combination of components described herein when provided to a subject was effective in controlling appetite and regulating weight and promoting weight loss of the subject. A subject taking the composition described herein once a day or twice a day for about 90 days may lose up to about 5 pounds in about 90 days, or up to about 10 pounds in 90 days, or up to about 15 pounds in 90 days, or up to about 20 pounds in 90 days, or up to about 25 pounds in 90 days, or up to about 30 pounds in 90 days, or any range or variation thereof. A subject taking the composition described herein once a day or twice a day for about 90 days may lose at least about 5 pounds in about 90 days, or at least about 10 pounds in about 90 days, or at least about 15 pounds in about 90 days, or at least about 20 pounds in about 90 days, or at least about 22 pounds in about 90 days, or up to about 25 pounds in about 90 days, or up to about 30 pounds in about 90 days, or greater than about 30 pounds in about 90 days, or any range or variation thereof. A subject taking the composition described herein once a day or twice a day for about 60 days may lose at least about 5 pounds in 60 days. A subject taking the composition described herein once a day or twice a day for about 60 days may lose at least 10 pounds in about 60 days, or at least about 15 pounds in about 60 days, or up to about 20 pounds in about 60 days, or greater than about 20 pounds in about 60 days, or any range or variation thereof. A subject taking the composition described herein once a day or twice a day for about 90 days may lose up to about 1% body fat pounds in about 90 days, or up to about 2% body fat pounds in about 90 days, or up to about 3% body fat pounds in about 90 days, or up to about 4% body fat pounds in about 90 days, or up to about 5% body fat pounds in about 90 days, or up to about 6% body fat pounds in about 90 days, or up to about 7% body fat pounds in about 90 days, or up to about 8% body fat pounds in about 90 days, or up to about 9% body fat pounds in about 90 days, or up to about 10% body fat pounds in about 90 days, or any range or variation thereof.

In addition, all subjects acknowledged having more energy, feeling more wakeful (more alert, e.g., in the morning and throughout the day), eating less and feeling full after eating less food, having less urge or desire to snack between meals, having fewer if no cravings for fatty or carbohydrate rich foods, having an overall better feeling of self, and sleeping better.

In many embodiments, the novel composition will be provided at an effective amount or therapeutically effective amount, which refers to that amount of the novel composition on its whole which, when administered to the subject, such as one in need thereof, is sufficient to effect at least a control and/or regulation of appetite.

Any novel composition described herein may also provide, at an effective amount or therapeutically effective amount, a control in weight (weight maintenance). Any of the novel compositions described herein may also provide, at an effective amount or therapeutically effective amount, a loss in weight.

The novel composition may also provide, at an effective amount or therapeutically effective amount, an improvement in sensation of satiation after eating a meal. The novel composition may also provide, at an effective amount or therapeutically effective amount, an improvement in mental clarity. The novel composition may also provide, at an effective amount or therapeutically effective amount, an improvement in overall sense of well-being, in level of energy and/or wakefulness. The novel composition may also provide, at an effective amount or therapeutically effective amount, an improvement in or feeling of restfulness after sleep. The novel composition may also provide, at an effective amount or therapeutically effective amount, a reduction in perception of or symptoms associated with stress and/or anxiety and/or depression. The novel composition may also provide, at an effective amount or therapeutically effective amount, a reduction in perception of or symptoms associated with fatigue. The novel composition may also provide, at an effective amount or therapeutically effective amount, a reduction in cravings for foods, such as cravings between meals, including reduction in craving for foods high in fats and/or carbohydrates. The novel composition may also provide, at an effective amount or therapeutically effective amount, a reduction in amount of food eaten during a meal, including a feeling of satiation from less food intake (relative to prior food intake on average for a given meal). Said effective amounts are as herein described. The amount that constitutes a "therapeutically effective amount" will vary depending on the exact composition, the subject (e.g., age, health, weight), and/or a weight loss goal established for the subject, but can be determined routinely by one of ordinary skill in the art having regard to his own knowledge and to this disclosure.

The formulations described herein may conveniently be presented in a unit dosage form or in a plurality of unit dosage forms or in bulk. Also provided are kits that will include one or more of the novel compositions described herein. A kit may include one or more additional agents or compounds with the described novel compositions described herein. The kit may include instructions for use. Some or all of the plurality components may be provided in different containers. The kit may be compartmentalized to receive the one or more containers in close confinement. Illustrative examples of containers for said kits include, but are not limited to, small glass containers, plastic containers, composite containers, straw-shaped plastic or paper containers, strips of plastic or paper, etc. Containers may be those that allow a worker or user to efficiently transfer components or accompanying reagents from one compartment to another. Such containers may also be ones that will accept a compound or compositions described herein, and/or may accept a resuspending solution. Said compositions may be in any of a powder (e.g. a lyophilized powder), precipitate, solid, gel, or liquid form, as examples. Compositions described herein or one or more of the components that make up the described novel compositions may be provided in the same or different forms in a single kit, and may be provided in the same or different containers.

With the compositions described herein, at least digestion, fat cell metabolism, neurotransmission, and endocrine activity are modulated and/or affected. The described composition having natural components and multiple targets provide a balanced and whole body approach to weight management. In combination, the components provided in the described compositions provide a plurality of activities, including neural effects for neural control/regulation of appetite, digestive effects and hormonal effects for control/regulation of satiation. The described novel compositions will in one or more forms also enhance mental performance (e.g., focus and/or memory). The multi-targeted approach with any composition described herein is not found when said individual components are taken independently from each other. The multi-targeted approach as described herein is not found in alternative compositions having a singular targeted approach. The components in the described compositions are provided in amounts that are acceptable for consumption. The described novel compositions will in one or more forms reduce unintended consequences associated with many current or alternative singular treatments for weight management and appetite control. These and other needs are met by the compositions described below.

The unique compositions described herein are formulated for the nutritional management of obesity and metabolic syndrome, by providing a balanced biology to the person treated with or administered any of the unique compositions described herein. Said compositions described herein target a plurality of anatomical systems and thereby affect the sensory system, digestive system, fat metabolism or lipolysis, cellular metabolism, and the endocrine system. Thus, as described herein, and not found in alternative formulations, is a composition containing components that target a plurality of specific neuropathways in the brain while simultaneously affecting behavioral patterns associated with eating (e.g., enhancing satiation, reducing cravings, minimizing overeating, triggering reward mechanisms, enhancing energy, improving wakefulness, reducing sensations of anxiety and/or depression, improving feeling of well-being) and overall metabolism. The plurality of botanical substances, in combination with the plurality of amino acids and nutrients in the compositions described herein provide maximum brain cell support for neural pathways involved in appetite control and hormone regulation. The compositions described herein restore and maintains a balance between principle neurotransmitters that regulate food intake while helping the person feel rewarded with less food. The compositions described herein also provides some critical and/or beneficial nutritional components to satisfy and maximize cellular energy functions, helping to reduce symptoms of depression and anxiety which contribute to hunger, cravings, and snacking. The amino acids included with the compositions described herein help to ensure maintenance of or maximum precursor supply for neurotransmitter production that supports key brain regions responsible for controlling hunger and/or snacking by increasing the feeling of satiety, reducing symptoms of depression and anxiety as well as improving focus and memory.

With the compositions described herein, and not found in alternative formulations, is the ability to modulate and/or regulate the degree to which many of the plurality of targeted pathways are specifically targeted, by adjusting one or a plurality of components in the composition to heighten or reduce said specific neuropathways in the brain while simultaneously or alternatively affecting the behavioral patterns described above associated with eating and/or the influence on metabolism. Thus, the support for or the neural pathways involved in appetite control and hormone regulation may be modified, for example, to promote weight maintenance rather than weight loss or may be modified to further influence focus and memory, to further influence energy and/or wakefulness, to further influence behavior related to hunger, cravings, and snacking, and/or to further influence behavior and/or feelings related to depression and/or anxiety, as representative examples.

Embodiments described herein include providing said novel compositions to a subject or to subjects. A subject may be a mammal, including an animal or other multicellular organism. A subject may be a human. A subject may be an animal, such as a pet or farm animal.

As used herein and in the appended claims, the singular forms "a," "and," and "the" include plural referents unless the context clearly dictates otherwise. Thus, for example, reference to "an agent" or to "a composition" includes a plurality of such agents or compositions, and equivalents thereof known to those skilled in the art, and so forth. It is understood that the term "comprising" (and related terms such as "comprise" or "comprises" or "having" or "including") is not intended to exclude embodiments wherein, for example, any composition of matter, composition, method, or process, or the like, described herein may "consist of" or "consist essentially of" the described features.

Although representative processes and articles have been described in detail herein, those skilled in the art will recognize that various substitutions and modifications may be made without departing from the scope and spirit of what is described and defined by the appended claims.

What is claimed is:

1. A composition for providing a multifaceted approach to appetite regulation, the composition having a plurality of differing components together in a dosing unit, in which at least some of the plurality of differing components target differing biologic pathways in a biologic system for regulation of appetite, including regulation of appetite at a meal and improving satiation between meals, the composition consisting of:
    a sufficient amount of an extract from a flower, or portions thereof, of *Crocus sativus* containing one or more from a group including safranal and crocin;
    a sufficient amount of an extract from a root of *Rhodiola rosea* containing more than one from a group consisting of rosavin, rosarin, rosin, salidroside with or without p-tyrosol, rhodioniside, rhodiolin, rosiridin, polyphenol, phenol, terpenoid, flavenoid, anthraquinone, and phenocarbonic acid;
    a sufficient amount of a co-combination, the co-combination containing a blend of purified saponin-containing fractions from a root of *Astragalus membranaceus* and a root of *Panax notoginseng*, the co-combination, together, in a pre-blended ratio that is between about 0.9:1 and 1:0.9 for the saponin-containing fraction from the root of *Astragalus membranaceus* and the saponin-containing fraction from the root of *Panax notoginseng*, respectively;
    a sufficient amount a plurality of amino acids or primary amines, each in at least one or both of a form and structure for human consumption, the plurality of amino acids or primary amines including at least two or more from a group including tyrosine, acetyl L-tyrosine, phenylalanine, DL phenylalanine, theanine, hydroxytryptophan (5-HTP), and phenylethylamine;
a sufficient amount of at least one metal in at least one of a form and structure for human consumption, wherein the at least one metal is selected from at least one of calcium in a form for human consumption; and
a sufficient amount of one or more vitamins, wherein the one or more vitamins are at least in one or both of a form and structure for human consumption; and
a sufficient amount of more than one pharmaceutically acceptable excipients, wherein the more than one pharmaceutically acceptable excipients are at least in one or both of a form and structure for oral consumption;
wherein the composition, prepared as a blend, and prior to providing for the regulation of appetite, being at least granulated, and
wherein the dosing unit is for oral delivery.

2. The composition of claim 1, wherein, in the composition,
the extract from the flower, or portions thereof, of *Crocus sativus*, the extract from the root of *Rhodiola rosea*, and the co-combination, together, is up to about 13% by weight based on the total weight of the composition;
the plurality of amino acids or primary amines are acetyl L-tyrosine, DL phenylalanine, theanine, hydroxytryptophan, and phenylethylamine, and, together, is up to about 50% by weight based on the total weight of the composition; and
the one or more vitamins are vitamin B-6 and vitamin B-12, and, together, is up to about 1% by weight based on the total weight of the composition.

3. The composition of claim 1, wherein, in the composition,
the extract from the flower, or portions thereof, of *Crocus sativus*, the extract from the root of *Rhodiola rosea*, and the co-combination, together, is up to about 4% by weight based on the total weight of the composition;
the plurality of amino acids or primary amines are acetyl L-tyrosine, DL phenylalanine, theanine, hydroxytryptophan, and phenylethylamine, and, together, is up to about 15% by weight based on the total weight of the composition; and
the one or more vitamins are vitamin B-6 and vitamin B-12, and, together, is less than 0.5% by weight based on the total weight of the composition.

4. The composition of claim 1, wherein the more than one pharmaceutically acceptable excipients comprise, in total, between about 30 wt. % and about 35 wt. % of the composition based on the weight of the composition.

5. The composition of claim 1, wherein the one or more vitamins are all or some of a B vitamin, the B-vitamin selected from the group consisting of vitamin B-3, vitamin B-6 and vitamin B-12.

6. The composition of claim 1, wherein the at least one metal is in a suitable valence that prevents toxicity in the biologic system after the oral delivery.

7. The composition of claim 1, wherein the dosing unit is in dry form.

8. The composition of claim 1, wherein the plurality of amino acids or primary amines include acetyl L-tyrosine, DL phenylalanine, theanine, hydroxytryptophan, and phenylethylamine.

9. The composition of claim 1, wherein the sufficient amount of more than one pharmaceutically acceptable excipients are at least one sweetener and at least one filler.

10. The composition of claim 1, wherein the sufficient amount of more than one pharmaceutically acceptable excipients are at least one non-sugar sweetener and at least one filler.

11. The composition of claim 1, wherein in the composition, components, comprising the sufficient amount of the extract from the flower, or portions thereof, of *Crocus sativus*, the sufficient amount of the extract from the root of *Rhodiola rosea*, the sufficient amount of the co-combination, the sufficient amount of the plurality of amino acids or primary amines, the sufficient amount of the at least one metal, the sufficient amount of the one or more vitamins, and the sufficient amount of more than one pharmaceutically acceptable excipients, together comprise up to about 21% of the composition based on the weight of the composition.

12. The composition of claim 1, wherein in the composition, components, comprising the sufficient amount of the extract from the flower, or portions thereof, of *Crocus sativus*, the sufficient amount of the extract from the root of *Rhodiola rosea*, the sufficient amount of the co-combination, the sufficient amount of the plurality of amino acids or primary amines, the sufficient amount of the at least one metal, the sufficient amount of the one or more vitamins, and the sufficient amount of more than one pharmaceutically acceptable excipients, together comprise up to about 67% of the composition based on the weight of the composition.

13. The composition of claim 1, wherein the co-combination is blend of a purified saponin-containing fraction from the root of *Astragalus membranaceus* containing one or more cycloartane glycoside compounds, and a purified saponin-containing fraction from the root of *Panax notoginseng* containing one or more ginsenoside or dammarane compounds.

14. The composition of claim 1, wherein the more than one pharmaceutically acceptable excipients comprise, in total, between about 75 wt. % and about 85 wt. % of the composition based on the weight of the composition.

15. A composition for providing a multifaceted approach to appetite regulation, the composition having a plurality of differing components together in a dosing unit, in which at least some of the plurality of differing components target differing biologic pathways in a biologic system for regulation of appetite, including regulation of appetite at a meal and improving satiation between meals, the composition consisting of:
a sufficient amount of an extract from a flower, or portions thereof, of *Crocus sativus* containing one or more from a group including safranal and crocin;
a sufficient amount of an extract from a root of *Rhodiola rosea* containing more than one from a group consisting of rosavin, rosarin, rosin, salidroside with or without p-tyrosol, rhodioniside, rhodiolin, rosiridin, polyphenol, phenol, terpenoid, flavenoid, anthraquinone, and phenocarbonic acid;
a sufficient amount of a co-combination, the co-combination containing a blend of purified saponin-containing fractions from a root of *Astragalus membranaceus* and a root of *Panax notoginseng*, the co-combination, together, in a pre-blended ratio that is between about 0.9:1 and 1:0.9 for the saponin-containing fraction from the root of *Astragalus membranaceus* and the saponin-containing fraction from the root of *Panax notoginseng*, respectively;
a sufficient amount a plurality of amino acids or primary amines, each in at least one or both of a form and structure for human consumption, the plurality of amino acids or primary amines including at least two or more from a group including tyrosine, acetyl L-tyrosine, phenylalanine, DL phenylalanine, theanine, hydroxytryptophan (5-HTP), and phenylethylamine;

a sufficient amount of at least one metal in at least one of a form and structure for human consumption, wherein the at least one metal is selected from at least one of calcium in a form for human consumption; and a sufficient amount of one or more vitamins, wherein the one or more vitamins are at least in one or both of a form and structure for human consumption;

a sufficient amount of caffeine in at least one of a form and structure for human consumption; and a sufficient amount of more than one pharmaceutically acceptable excipients, wherein the more than one pharmaceutically acceptable excipients are at least in one or both of a form and structure for oral consumption;

wherein the composition, prepared as a blend, and prior to providing for the regulation of appetite, being at least granulated, and wherein the dosing unit is for oral delivery.

16. The composition of claim 15, wherein the sufficient amount of caffeine is in an amount between about 10 mg and about 100 mg.

17. The composition of claim 15, wherein the more than one pharmaceutically acceptable excipients comprise, in total, between about 30 wt. % and about 35 wt. % of the composition based on the weight of the composition.

18. The composition of claim 15, wherein the more than one pharmaceutically acceptable excipients comprise, in total, between about 75 wt. % and about 85 wt. % of the composition based on the weight of the composition.

19. The composition of claim 15, wherein the more than one pharmaceutically acceptable excipients comprise, in total, between about 30 wt. % and about 35 wt. % of the composition based on the weight of the composition, and the more than one pharmaceutically acceptable excipients include a sweetener, dicalcium phosphate, microcrystalline cellulose, hydroxypropyl methylcellulose, magnesium stearate, silica, croscarmellose sodium, and stearic acid.

20. The composition of claim 15, wherein the more than one pharmaceutically acceptable excipients comprise, in total, between about 75 wt. % and about 85 wt. % of the composition based on the weight of the composition, and the more than one pharmaceutically acceptable excipients include a sweetener, soluble fiber, a buffering acid, and silica.

21. The composition of claim 15, wherein the dosing unit is in dry form.

22. The composition of claim 15, wherein, in the composition,
the one or more vitamins are vitamin B-6 and vitamin B-12;
the plurality of amino acids or primary amines are acetyl L-tyrosine, DL phenylalanine, theanine, hydroxytryptophan, and phenylethylamine; and
the calcium in a form for human consumption is in a suitable valence that prevents toxicity in the biologic system after the oral delivery.

23. The composition of claim 15, wherein, in the composition,
the one or more vitamins are vitamin B-6 and vitamin B-12; and
the plurality of amino acids or primary amines are acetyl L-tyrosine, DL phenylalanine, theanine, hydroxytryptophan, and phenylethylamine.

* * * * *